United States Patent
Ben-Oren et al.

(10) Patent No.: US 7,338,444 B2
(45) Date of Patent: *Mar. 4, 2008

(54) MANAGEMENT OF GASTRO-INTESTINAL DISORDERS

(75) Inventors: Ilan Ben-Oren, Jerusalem (IL); Julian Daich, Jerusalem (IL); Ephraim Carlebach, Raanana (IL); George Yariv, Jerusalem (IL)

(73) Assignee: Oridion Breathid Ltd, Jerusalem (IL)

( * ) Notice: Subject to any disclaimer, the term of this patent is extended or adjusted under 35 U.S.C. 154(b) by 67 days.

This patent is subject to a terminal disclaimer.

(21) Appl. No.: 10/519,723

(22) PCT Filed: Mar. 6, 2003

(86) PCT No.: PCT/IL03/00178

§ 371 (c)(1),
(2), (4) Date: Jul. 26, 2005

(87) PCT Pub. No.: WO2004/002308

PCT Pub. Date: Jan. 8, 2004

(65) Prior Publication Data

US 2006/0074335 A1 Apr. 6, 2006

(30) Foreign Application Priority Data

Aug. 22, 2002 (WO) .................. PCT/IL02/00702

(51) Int. Cl.
*A61B 5/00* (2006.01)
*A61B 5/08* (2006.01)
*A61B 5/103* (2006.01)

(52) U.S. Cl. .................. 600/300; 600/532; 600/593

(58) Field of Classification Search ............ 600/300, 600/301, 529, 531, 532, 543, 587, 593, 30
See application file for complete search history.

(56) References Cited

U.S. PATENT DOCUMENTS 6,548,043 B1 * 4/2003 Wagner et al. ............. 424/1.81
6,740,305 B1 * 5/2004 Ajami ....................... 424/9.1

OTHER PUBLICATIONS

Kuiken et al. "Development of a test to measure gastric accommodation in humans" Am J Physiol Liver Physiol 277:1217-1221; 1999. Accessed Sep. 27, 2007 at ajpgi.physiology.org.*

* cited by examiner

*Primary Examiner*—Charles A. Marmor, II
*Assistant Examiner*—Patricia C Mallari
(74) *Attorney, Agent, or Firm*—EMPK & Shiloh, LLP

(57) ABSTRACT

The present invention relates to the field of methods and apparatus for the determination of various conditions of gastric and gastro-intestinal malfunction, especially those performed by means of breath tests.

28 Claims, 18 Drawing Sheets

FIG. 7

| SUBJECT STATUS | TWO MEAL PROCEDURE | | | | | | TWO TEST PROCEDURE | | | | | |
|---|---|---|---|---|---|---|---|---|---|---|---|---|
| | $t_{1/2}$ | | | $t_{lag}$ | | | $t_{1/2}$ | | | $t_{lag}$ | | |
| | FIRST (MIN) | SECOND (MIN) | DEVIATION (%) | FIRST (MIN) | SECOND (MIN) | DEVIATION (%) | FIRST (MIN) | SECOND (MIN) | DEVIATION (%) | FIRST (MIN) | SECOND (MIN) | DEVIATION (%) |
| ASYMPTOMATIC | 107.2 | 97.2 | 9.35 | 69.2 | 52.6 | 23.4 | 100.8 | 91.4 | -10.3 | 44.6 | 46.6 | 4.2 |
| SYMPTOMATIC | 154.1 | 99.5 | 35.4 | 95.1 | 56.4 | 40.7 | 155.5 | 99.3 | 36.1 | 87.3 | 55.7 | 36.2 |
| SYMPTOMATIC | 173.9 | 111.8 | 35.7 | 90.1 | 52.2 | 42.0 | 204.8 | 120.6 | 41 | 112 | 76.1 | 31.8 |
| SYMPTOMATIC | 128.3 | 91.4 | 28.8 | 68.4 | 45.8 | 33.8 | | | | | | |
| ASYMPTOMATIC | 89.3 | 92.3 | -3.3 | 55.1 | 41.6 | 24.5 | | | | | | |
| ASYMPTOMATIC | 102.2 | 113.6 | -11.1 | 65.8 | 57.2 | 13.1 | | | | | | |

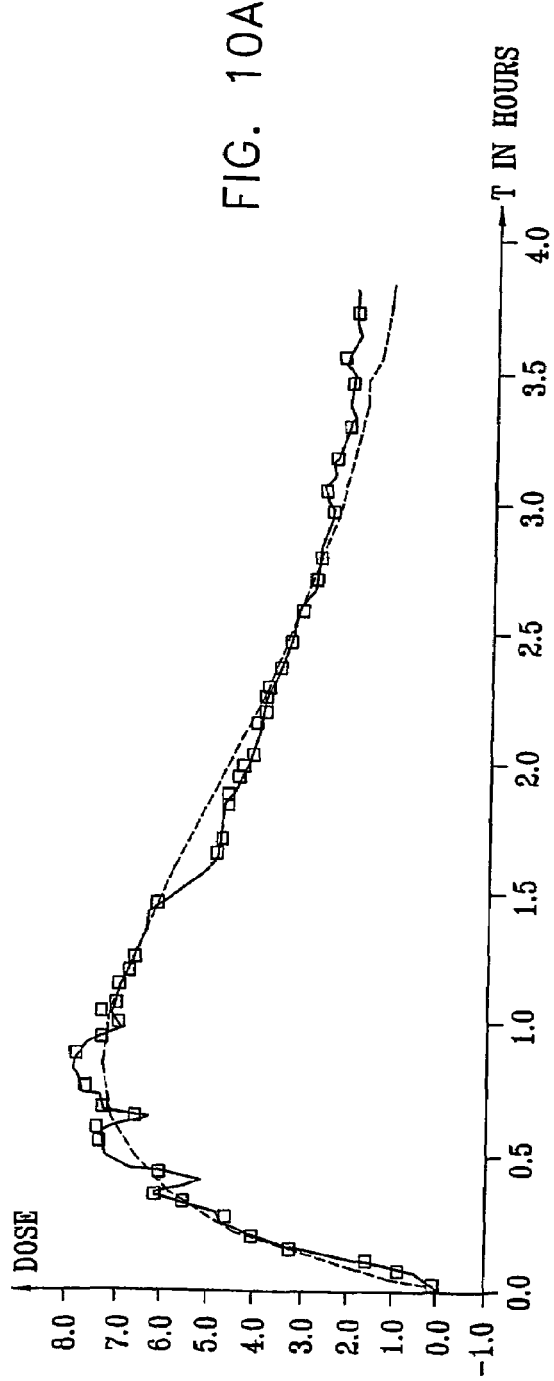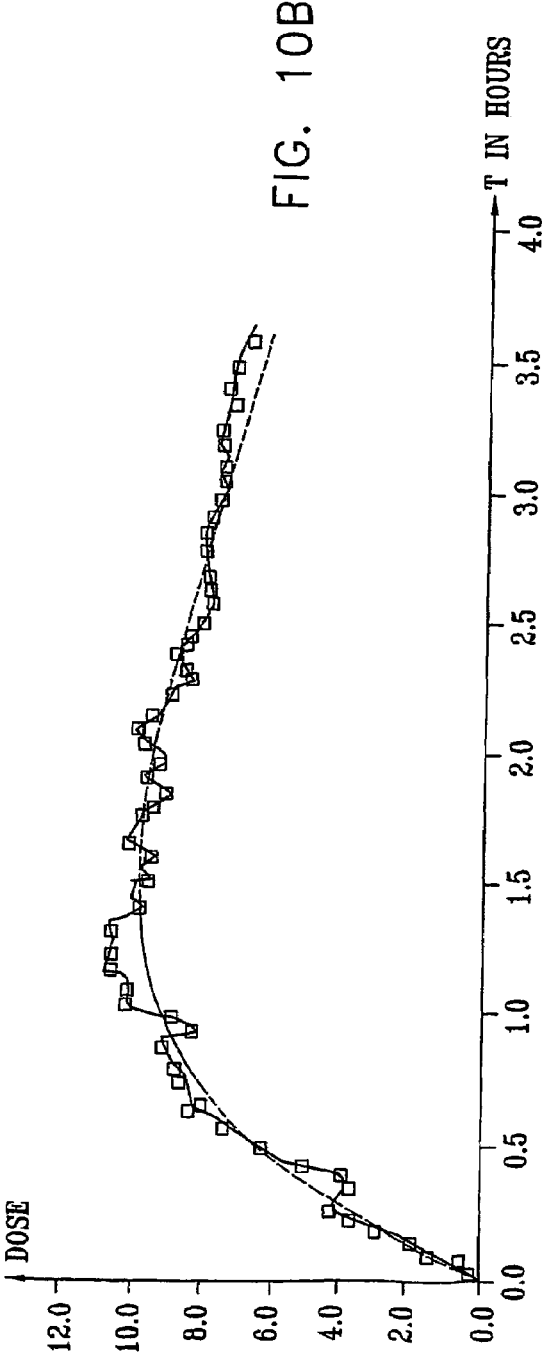
FIG. 10A
FIG. 10B

MANAGEMENT OF GASTRO-INTESTINAL DISORDERS

FIELD OF THE INVENTION

The present invention relates to the field of methods and apparatus for the determination of various conditions of gastric and gastrointestinal malfunction, especially those performed by means of breath tests.

BACKGROUND OF THE INVENTION

It is estimated that more than 25% of the general population in developed countries suffer from different degrees of functional dyspepsia and/or Irritable Bowel Syndrome, IBS. Such conditions are called for the purposes of this application, functional GI disorders. These disorders are clinical syndromes characterized by GI symptoms without identifiable cause. When a physiological cause is identified, these disorders are more correctly called organic dyspepsia or bowel disorders. The complex of dyspeptic symptoms is usually related to pain or discomfort generally felt in the center of the abdomen around or above the navel. Some examples of discomfort include fullness, early satiety, which is a feeling of fullness soon after starting to eat, bloating and nausea. There is no single organic disorder that explains all these symptoms, although about a third of all patients with these symptoms have delayed gastric emptying, though not usually so severe that it causes frequent vomiting. Additionally, a third also show a failure of the relaxation of the upper stomach following an ingestion of food, a condition known as abnormal gastric accommodation reflex. The prevalence of delayed gastric emptying in these patients is not significantly higher compared to asymptomatic individuals, but about half of the patients with these symptoms also have a sensitive or irritable stomach which causes sensations of discomfort when the stomach contains even small volumes. A gastric emptying study can show whether there is poor emptying of the stomach. Other motility disorders are more difficult to detect, but recently, there has been developed, as described for instance in "Practical Guide to Gastrointestinal Function Testing", by C. Stendal, pages 194-201, published by Blackwell Science Ltd, Oxford, U.K., (1997), methods using an intragastric balloon connected to a computer-controlled pump called a barostat, which can show:

(a) distention or whether the upper stomach relaxes adequately during eating, and
(b) how much filling of the stomach it takes to cause pain or discomfort or gastric accommodation.

Barostat studies have shown the relation between dyspepsia symptoms and impaired accommodation by means of measuring stomach volumes as a function of intra-gastric pressure, or vice versa, and/or the symptomatic response to changes in intragastric pressure at different gastric volumes. In such barostat procedures, a liquid meal is administered, which can be either a high volume of water (up to 2 liters), an isotonic or high caloric value solution such as Ensure or Gatorade, a soup or a glucagon infusion. Then, for a given volume of the balloon, the pressure needed to induce gastric discomfort or pain is measured. This method is invasive, uncomfortable to the patient and impractical for wide clinical use. Furthermore, the barostat bag may interfere with gastric motility resulting in an inaccurate result. Another example of an organic cause of dyspepsia is a *Helicobacter pylori* infection.

Asymptomatic patients in risk groups such as diabetic patients, patients under drug therapy for Parkinson's Disease, and others, also benefit from investigations for determining specific GI disorders, which can affect the prognosis of their main diseases. For example, disturbed gastric emptying may affect the glycemic control in diabetic patients.

The stomach is generally described as being divided into two separate autonomic parts—the upper, proximal or fundus, and the lower, distal or antrum. The upper (proximal/fundus) stomach distends on the entry of food, as well as acting as a food reservoir and as a pump that pushes the liquids and gastric contents out of the stomach. The function of the lower (distal/antrum) stomach is to grind food down to smaller particles and mix it with digestive juices so that it can be absorbed when it reaches the small intestine. The stomach also empties its contents into the intestine at a controlled rate to avoid excessive delivery of food or acids, which could damage or overload the small intestine.

Three types of movements can generally be discerned in the stomach:

1. Rhythmic, synchronized contractions in the lower part of the stomach, at a rate of approximately 3 per minute, which create waves of food particles and juice which splash against the closed sphincter muscle (the pyloric sphincter) to grind the food down into small particles.
2. The upper part of the stomach shows slow relaxations lasting a minute or more that follow each swallow and that allow the food to enter the stomach maintaining constant pressure while volume is changing; at other times the upper part of the stomach shows slow contractions creating a gradient in pressure, which help to empty the stomach.
3. Between meals, after all the digestible food has left the stomach, there are occasional bursts of very strong, synchronized contractions that are accompanied by opening of the pyloric sphincter muscle. These are sometimes called "house-keeper waves" because their function is to sweep any indigestible particles out of the stomach. Another name for them is the migrating motor complex.

As previously mentioned, the barostat method is invasive, uncomfortable, impractical for wide clinical use, and may not necessarily provide accurate results. Furthermore, it is limited to determination of distension and filling disorders of the stomach alone, and other tests need to be applied for other disorders manifesting themselves in the GI tract, such as those generically related to transit time or malabsorption, or those called IBS disorders. The widespread prevalence of such gastric and GI malfunction makes it important to have a simple, quick, easily tolerable and reliable test for diagnosing and discriminating between various forms of such disorders.

The above-referenced book by C. Stendal is particularly useful as a review of the background of the subject matter of this application. The disclosures of each of the publications mentioned in this section and in other sections of the specification, are hereby incorporated by reference, each in its entirety.

SUMMARY OF THE INVENTION

The present invention seeks to provide new apparatus and kits for use in implementing novel methods, that allow a more exact diagnosis of gastric disorders in patients that suffer from dyspepsia or IBS, as well as in asymptomatic patients that are in risk groups. In particular, methods are proposed that allow a more exact diagnosis by means of dedicated breath tests for GI disorder determination. When these methods are implemented in the form of breath tests, they are also easily tolerated by the patient, and sufficiently simple that they can be performed by medical technicians, in contrast to many of the prior art tests for gastric disorders, which could be performed only by medical doctors. An automated breath tester which provides real time results, such as that described in U.S. Pat. No. 6,186,958 for "Breath Test Analyzer", assigned to the assignee of the present invention, not only make the tests quicker, but also is almost essential for enabling the practical execution of some of the methods of the present invention, where almost continuous, on-line monitoring of the results enables the tests to be completed sooner than in prior art methods where the provision of real time results is not feasible. However, the apparatus of the present invention, at least for implementing the methods of the present invention relating to gastric emptying and gastric accommodation, can also be of other types capable of following the gastro-intestinal progress of a meal. Other such types of apparatus for breath analysis, include isotope ratio mass spectrometers and others. Other types of instruments unrelated to breath tests, include an MRI imager, a Computerized Tomography System, a scintigraphic imager (a gamma camera), an X-ray apparatus, an ultrasound imager, or others, as described below. However, except where otherwise noted, and in order to simplify the application, the apparatus generally used to describe the various embodiments of this invention is a breath test apparatus.

In addition, the preferred methods and apparatus of the present invention allow control management of the treatment of such patients. The significant clinical advantage of these methods is clear, due to recent research work that shows that GI patients often have symptoms that are not stable; therefore treatment according to symptoms only, without ongoing testing, may be problematic.

The disorders that can be diagnosed and followed by the preferred methods and apparatus of the present invention can be divided into two groups:

(A) Dyspepsia-type disorders, generally related to feelings in the region of the stomach, including
  (i) delayed gastric emptying;
  (ii) disturbed gastric accommodation;
  (iii) the effects of *Helicobacter pylori* infection; and
  (iv) gastric chemical sensitivity or sensation.

(B) Irritable Bowel Syndrome type disorders, including:
  (v) bacterial overgrowth;
  (vi) lactose intolerance; and
  (vii) orocecal transit time disorders.

The assessing of different physiological findings for dyspepsia, allows the prescription of the appropriate therapy. For example, a patient with delayed gastric emptying and normal gastric accommodation can be treated with prokinetic therapy (including pharmacological agents, diet). In another example, a patient with abnormal gastric accommodation and a positive urea breath test for *H. pylori* can be treated for *H. pylori* eradication alone or in combination with a fundus-relaxing drug.

There is further provided in accordance with yet another preferred embodiment of the present invention a set of at least one meal, at least one meal of the set comprising at least one constituent operative to cause retention of the at least one meal in the stomach of a subject, and having a predetermined volume, for use in determination of gastric accommodation of the subject by means of at least two measurements of a gastric emptying parameter of the at least one meal as a function of the volume of the meal having exited the stomach of the subject. Preferably, the at least one meal is one meal, and the at least two measurements are performed on the one meal. Furthermore, at least one of the at least two measurements is performed on a liquid emptying phase of the meal from the stomach of the subject. Additionally, the at least one meal is at least two meals, and one of the at least two measurements is performed on a first one of the at least two meals, and a second one of the at least two measurements is performed on a second one of the at least two meals. The first one of the at least two meals may be larger than the second one of the at least two meals, or smaller.

In the above-mentioned preferred embodiments of the present invention, the predetermined volume is at least 150 milliliters, and at least one meal of the set comprises a marker which is detected after leaving the stomach of the subject. This marker may preferably be detected by its presence in the exhaled breath of the subject, or within the body of the subject, in which case it may be preferably detected by its presence in the gastro-intestinal tract of the subject.

In the above mentioned embodiments of the present invention, at least one meal of the set preferably comprises at least one of:
  a caloric value of at least 150 kcalories,
  a lipid content of at least 5%,
  a carbohydrate content of at least 10%,
  a protein content of at least 5%, and
  a pH value of less than 3.

The carbohydrate may preferably be glucose.

In accordance with yet another preferred embodiment of the present invention, there is provided a single-dosage liquid meal for use by a subject in a breath test, comprising,
  (i) a volume of at least 500 milliliters,
  (ii) an agent causing gastric retention of the meal, and
  (iii) a marker, stable in the gastric environment, and detectable upon exiting the stomach of the subject.

The agent causing gastric retention of the meal may preferably comprise at least one of:
  (i) a caloric value of at least 150 kcalories,
  (ii) a lipid content of at least 5%,
  (iii) a carbohydrate content of at least 10%,
  (iv) a protein content of at least 5%, and
  (v) a pH value of less than 3.

There is further provided in accordance with yet another preferred embodiment of the present invention apparatus for determining the gastric accommodation of a subject, following sequential administration to the subject of a first and a second meal, at least one of the meals comprising a marker detectable upon exiting the stomach of the subject, the apparatus comprising:
  a detector for detecting the marker upon exiting the stomach of the subject, and providing a marker output signal conveying information about the rate of emptying of the meal from the stomach of the subject, and
  a data processing system receiving the marker output signal and calculating a first set of parameters which characterizes the gastric emptying of the first meal, and a second corresponding set of parameters which characterizes the gastric emptying of the second meal, and which determines the gastric accommodation by comparing two corresponding parameters from the first and the second sets of parameters. In using this apparatus, the first and the second meals may be of different volumes, in which case the gastric accommodation is determined from the dependence of the parameters on the volumes of the first and second meals. Alternatively and preferably, the first and the second meals may be of similar volumes, and the second meal is administered before the first meal has emptied from the stomach of the subject.

In any of the last mentioned apparatus embodiments, the processing system may preferably be such as to compare a set of parameters of the second meal before the first meal has emptied from the stomach of the subject. Furthermore, the marker is preferably detected by its presence in the exhaled breath of the subject or within the body of the subject, and if so, preferably by its presence in the gastro-intestinal tract of the subject.

In the above mentioned apparatus, the set of parameters calculated by the processing system preferably comprises at least one of $t_{1/2}$, $t_{lag}$, GEC, CPDR, and the integral under a plot of the DoB as a function of time.

In accordance with still another preferred embodiment of the present invention, there is provided a kit for the diagnosis of gastric accommodation in a subject, comprising:
(i) a quantity of material for marking a first meal having a first predetermined volume and a first predetermined gastric retention characteristic,
(ii) a quantity of material for marking a second meal having a second predetermined volume and a second predetermined gastric retention characteristic, and
(iii) a protocol providing information relating to the preparation of the first meal and of the second meal.

The protocol may also preferably provide information relating to the administration of the first and the second meals to the subject, and may also provide information relating to the point in time when the second meal is taken, according to the results of gastric emptying measured on the first meal. The kit may also comprise the material necessary for the preparation of at least one of the meals, and also may include a breath collecting device, which is generally a disposable device.

There is further provided in accordance with still another preferred embodiment of the present invention, a breath test apparatus for determining at least one gastrointestinal condition in a subject, comprising:
(i) a breath collection device for collecting breath from a subject after ingestion of a marked substrate, and
(ii) a gas analyzer for detecting the products of the marked substrate in the exhaled breath of the subject, wherein the breath test apparatus and the marked substrate are adapted to perform a first breath test selected from a group of possible breath tests providing gastrointestinal information related to the subject, and wherein the breath test apparatus and the marked substrate are also adapted to perform at least a second breath test selected from the group of breath tests, according to the outcome of at least the first breath test, such that a gastro-intestinal condition of the subject is determined from the outcome of at least one of the breath tests.

In this breath test apparatus the gastro-intestinal condition may comprise at least one of dyspepsia and irritable bowel syndrome, and the dyspepsia may be such that arises from at least one of a gastric emptying disorder, a gastric accommodation disorder, and a *Helicobacter pylori* infection. Additionally, the irritable bowel syndrome may arise from at least one of a sugar malabsorption disorder, a bacterial overgrowth, and an orececal transit time disorder. In such a case, the sugar malabsorption disorder is at least one of lactose intolerance, fructose intolerance, sucrose intolerance and maltose intolerance.

In accordance with a further preferred embodiment of the present invention, there is also provided a breath test apparatus for the determination of gastric emptying of a subject, comprising:
(i) a gas collector, for collecting exhaled breath samples from the subject after administration of a test meal comprising a marker, whose by-products are exhaled in the breaths of the subject in accordance with the rate of emptying of the marker from the stomach of the subject,
(ii) a gas analyzer for analyzing the collected exhaled breath, wherein the analyzing is performed essentially continuously, and
(iii) a computing system which calculates, as the breath test proceeds, at least one of the $t_{1/2}$, $t_{lag}$, delta over baseline (DoB) curve amplitude, the integral under the plot of the DoB as a function of time, and Gastric Emptying Coefficient (GEC) parameters of the subject, wherein the breath test apparatus provides an indication of a gastric emptying disorder by determining a final estimated value of at least one of the parameters, and determining whether the parameter departs significantly from known norms for the value of the parameter. This apparatus is preferably such that an indication is provided of a gastric emptying disorder in the subject while the subject is still providing breath samples to the analyzer, or alternatively and preferably, in accordance with the on-going analyses of the breaths of the subject.

There is also provided in accordance with yet a further preferred embodiment of the present invention, a substrate for isotopic breath tests, comprising an isotopically labeled material in a micro-encapsulated coating material, wherein the properties of the micro-encapsulation coating material are chosen such that the isotopically labeled material is released in a predetermined part of the gastro-intestinal tract. The micro-encapsulation coating material is preferably chosen such that it breaks down and releases the isotopically labeled material according to the pH value of the environment through which it is passing. Alternatively and preferably, the material is such that it breaks down and releases the isotopically labeled material only after leaving the stomach of a subject. In the latter case, the isotopically labeled material may be used as a marker for determining passage through the duodenum. In accordance with further preferred embodiments of the present invention, the micro-encapsulation coating material is chosen such that it breaks down and releases the isotopically labeled material under the effect of enzymic action arising from the enzymic environment through which it is passing. The enzymes may preferably be those secreted by at least one of the pancreas and the gall bladder, such that the isotopically labeled material is used as a marker for determining passage through the duodenum.

In general, the micro-encapsulation coating is preferably such that it can be more readily bonded to an administered meal than the isotopically labeled material itself.

There is even further provided in accordance with a preferred embodiment of the present invention, a set of a first and a second liquid meal for use in determining the gastric accommodation of a subject, the first liquid meal comprising a first predetermined volume, and the second liquid meal comprising a second predetermined volume greater than the first predetermined volume and having a predetermined gastric retention characteristic, wherein the second liquid meal is administered to the subject after the first liquid meal has begun emptying from the stomach of the subject, and wherein the gastric accommodation of the subject is determined according to the deviation between a measured rate of emptying of the second meal and a measured rate of emptying of the first meal. Preferably, the second predetermined volume is sufficient to cause gastric distension in the subject, and may preferably be at least 500 milliliters of liquid. In the above-mentioned sets of meals, the gastric retention characteristic may be such as to arise from at least one of a predetermined pH, a predetermined calorific value and a predetermined composition of the second liquid meal. The predetermined pH is preferably less than 3.0, the predetermined calorific value is preferably at least 150 kilocalories, and the predetermined composition is preferably an isotonic composition. The second liquid meal is preferably administered as soon as the rate of emptying of the first meal from the stomach of the subject is determined, or may be administered after a time when essentially all physiological effects of the first meal on the subject have terminated. Alternatively, the second liquid meal is administered on a successive day to the first meal. Furthermore, the rate of emptying may be determined by any of a breath test, scintigraphy, an X-ray, computerized tomography, gamma imaging or an ultrasound method.

There is also provided in accordance with a further preferred embodiment of the present invention a liquid meal comprising a predetermined volume and having a predetermined gastric retention characteristic, for use in determining the gastric accommodation of a subject, wherein the average gastric emptying rate of the meal for a large plurality of normal subjects is known, and wherein the rate of emptying of the meal from the stomach of the subject is measured, and wherein the deviation between the rate of emptying of the meal from the stomach of the subject and the average rate of emptying of the meal for a large plurality of normal subjects, provides an indication of the gastric accommodation of the subject. Preferably, the predetermined volume is sufficient to cause gastric distension in the subject, and may be at least 500 milliliters of liquid. In the above mentioned liquid meal, the gastric retention characteristic may arise from at least one of a predetermined pH, a predetermined calorific value and a predetermined composition of the liquid meal. The predetermined pH may be less than 3.0, the predetermined calorific value may preferably be at least 150 kilocalories, and the predetermined composition is preferably an isotonic composition. Furthermore, the rate of emptying may be determined by any of a breath test, scintigraphy, an X-ray, computerized tomography, gamma imaging or an ultrasound method.

In accordance with yet another preferred embodiment of the present invention, there is provided an isotopically labeled liquid meal, comprising a predetermined volume and having a predetermined gastric retention characteristic, for use in determining the effect of the volume of a meal on the intragastric pressure of a subject, wherein the rate of emptying of the meal from the stomach of the subject is determined by means of a breath test performed to detect isotopically labeled products of the meal in the breath of the subject, for meals of varying predetermined volumes.

There is further provided in accordance with yet another preferred embodiment of the present invention, a meal administered to a subject, for use in the determination of gastrointestinal disorders in the subject, the meal comprising at least a first and a second marker material, the first material being such that it is not generally absorbed in the subject's stomach, and releases a predefined gas in the presence of intestinal bacteria, and the second material being such that it indicates a location of the meal within the gastro-intestinal tract of the subject, and wherein the generation of the predefined gas in the subject is detected by means of a breath test, and the position within the subject's gastro-intestinal tract at which the predefined gas is generated is determined by means of the second marker material. In the above-mentioned meal, a by-product of the second marker material may also be detected by means of a breath test, such that the position of the predefined gas generation in the gastro-intestinal tract of the subject is determined by the temporal relationship between the appearance of the predefined gas and of a by-product of the marker material in the subject's breath. The second marker material is preferably labeled with a carbon isotope, and the by-product is isotopically labeled carbon dioxide. Furthermore, the first material may preferably be a sugar metabolized in the small intestine of the subject, such that the time of detection of the predefined gas relative to the time of detection of the second marker material is used to determine the presence of bacterial overgrowth in the small intestine. In this case, the second material may also be a labeled sugar, also metabolized in the small intestine of the subject, such that the generally concurrent appearance in the breath of the subject of the predefined gas and a by-product of the second marker material may be indicative of the presence of bacterial overgrowth in the subject. Additionally, the second material may be a labeled sugar also metabolized in the small intestine of the subject, such that the appearance in the breath of the subject of a by-product of the second marker material significantly prior to the appearance of the predefined gas may be generally indicative of the absence of bacterial overgrowth in the subject. In the above-mentioned meals, the first material is preferably at least one of glucose and lactulose. The second material may be at least one of labeled sodium acetate, sodium octanoate, glucose, an acetyl leucine probe, or a microencapsulated labeled substrate.

In any of the above-mentioned meals, the first material is preferably a sugar generally metabolized in the small intestine of the subject, such that detection of the predefined gas essentially concurrent with detection of a small quantity of the second marker material may be used to determine the orocaecal transit time of the subject. Alternatively and preferably, the first material is a sugar of a group thought to be malabsorbed in the small intestine of the subject, such that it arrives essentially unabsorbed at the colon of the subject, where the predefined gas is generated by the presence of colonic bacteria, such that the time of detection of the predefined gas relative to the time of detection of the second marker material may be used to determine a sugar intolerance in the subject. Also, the second material may be an isotopically labeled material generally absorbed in the colon, such that detection of the predefined gas essentially concurrent with detection of labeled by-products of the second marker material is used to determine a sugar intolerance in the subject. The second material may then be xylose labeled with a carbon isotope, and the by-product is isotopically labeled carbon dioxide. Additionally, the second material may be an isotopically labeled material generally absorbed in the small intestine, such that the relative time and quantity of detection of the predefined gas and labeled by-products of the second marker material is used to determine whether the subject is suffering from one or both of a sugar intolerance and a bacterial overgrowth.

In accordance with still another preferred embodiment of the present invention, in the use of the above mentioned meals, the detection of a small quantity of the predefined gas, characteristic of a small part of the first material in the presence of bacteria, occurring essentially concurrently with the detection of the labeled by-products of the second marker material is used as an indication that the subject is suffering a bacterial overgrowth. The detection of the predefined gas later than the detection of the labeled by-products of the second marker material generally can be used to indicate that the subject is suffering from a sugar intolerance. The detection of a large quantity of the predefined gas, characteristic of the majority of the first material in the presence of bacteria, occurring essentially concurrently with the detection of the labeled by-products of the second marker material may preferably indicate that the subject is suffering a sugar intolerance and a bacterial overgrowth. In any of the above-mentioned meals, the sugar may preferably be at least one of the group consisting of lactose, fructose, maltose and sucrose. Furthermore, the predefined gas may be hydrogen and/or methane.

In accordance with yet another preferred embodiment of the present invention, there is provided a breath test apparatus comprising:
(i) a breath sample input port for receiving exhaled breath from a subject after administration to the subject of at least one meal, at least one of the at least one meal comprising a marker detectable upon exiting the stomach of the subject,
(ii) at least one gas analyzer for detecting the marker in the exhaled breath of the subject,
(iii) a gastric function processing module, receiving information from the at least one gas analyzer and determining at least one of the gastric emptying rate and the gastric accommodation of the subject,
(iv) dyspeptic symptom input functionality, receiving information from the subject about the level of dyspeptic symptoms perceived at least upon administration of the first meal and the second meal, and
(v) a gastrointestinal diagnostic processor, receiving information from the gastric function processing module and the dyspeptic symptom input functionality, and providing an output indicative of the visceral sensitivity of the subject.

In this breath tester, the at least one meal may preferably comprises at least a first and a second meal, at least one of the meals comprising a marker detectable upon exiting the stomach of the subject There is further provided in accordance with yet another preferred embodiment of the present invention breath test apparatus comprising:
(i) a breath sample input port for receiving exhaled breath from a subject after administration to the subject of at least one meal, at least one of the at least one meal comprising a marker detectable upon exiting the stomach of the subject,
(ii) at least one gas analyzer for detecting the marker in the exhaled breath of the subject,
(iii) a gastric function processing module, receiving information from the at least one gas analyzer and determining the gastric emptying rate and the gastric accommodation of the subject, and
(iv) a gastrointestinal diagnostic processor, receiving information from the gastric function processing module and providing an evaluation of at least two causes of functional gastro-intestinal disorders in a single procedure.

In this breath tester, the at least one meal may preferably comprises at least a first and a second meal, at least one of the meals comprising a marker detectable upon exiting the stomach of the subject In accordance with still another preferred embodiment of the present invention, there is provided more breath test apparatus comprising:

(i) a breath sample input port for receiving breath from a subject after administration to the subject of at least one meal, at least one of the at least one meal comprising a marker detectable upon exiting the stomach of the subject,
(ii) at least one gas analyzer for detecting the marker in the exhaled breath of the subject,
(iii) a gastric function processing module, receiving information from the at least one gas analyzer and determining at least one of gastric emptying rate and gastric accommodation of the subject,
(iv) dyspeptic symptom input functionality, receiving information from the subject about the level of dyspeptic symptoms perceived at least upon administration of the first meal and the second meal, and
(v) a gastrointestinal diagnostic processor, receiving information from the gastric function processing module and the dyspeptic symptom input functionality, and providing an evaluation of at least one cause of dyspepsia in a subject, the at least one cause being selected from gastric accommodation, gastric emptying and visceral sensitivity, in a single procedure.

In this breath tester, the at least one meal may preferably comprises at least a first and a second meal, at least one of the meals comprising a marker detectable upon exiting the stomach of the subject There is further provided in accordance with still another preferred embodiment of the present invention, a kit for use in a breath test for the evaluation of at least one of the causes of dyspepsia in a subject, comprising:
(i) a first quantity of material for marking a first meal having a first predetermined volume and a first predetermined gastric retention characteristic,
(ii) a second quantity of material for marking a second meal having a second predetermined volume and a second predetermined gastric retention characteristic, and
(iv) a protocol providing information relating to the preparation of the first meal and of the second meal,
(v) wherein the breath test evaluates at least one of the causes of dyspepsia in a subject selected, from gastric accommodation, gastric emptying and visceral sensitivity in a single procedure.

In the above-mentioned kit, the first predetermined volume and the second predetermined volume may preferably be different.

In accordance with a further preferred embodiment of the present invention, there is also provided a set of a first and a second meal for use in determining at least two of gastric accommodation, gastric emptying and visceral sensitivity of a subject, the first meal comprising a first predetermined volume, and the second liquid meal comprising a second predetermined volume and having a second predetermined gastric retention characteristic, wherein the second meal is administered to the subject after the first liquid meal has begun emptying from the stomach of the subject, and wherein the measured emptying rates of the first and second meal are utilized to determine the gastric emptying and gastric accommodation level of the subject, and wherein dyspeptic symptoms of the subject are ascertained at least upon administration of the first and the second meal, and wherein the dyspeptic symptoms of the subject are correlated with the volumes of the first and second meal to determine the level of visceral sensitivity, such that at least two of gastric accommodation, gastric emptying and visceral sensitivity of a subject may be determined in a single procedure.

In the above-mentioned set of a first and a second meal the first predetermined volume and the second predetermined volume may preferably be different.

There is provided in accordance with yet a further preferred embodiment of the present invention, a set of at least one meal, at least one meal of the set comprising at least one constituent operative to cause retention of the at least one meal in the stomach of a subject, and having a predetermined volume, for use in the determination of at least two of gastric accommodation, gastric emptying and visceral sensitivity of a subject, wherein the gastric accommodation and the gastric emptying are determined by making at least two measurements of a gastric emptying parameter of the at least one meal as a function of the volume of the meal having exited the stomach of the subject, and wherein dyspeptic symptoms of the subject are ascertained as a function of the volume of the meal retained in the stomach of the subject to determine the level of visceral sensitivity, such that at least two of gastric accommodation, gastric emptying and visceral sensitivity of a subject may be determined in a single procedure.

In the above-mentioned set of at least one meal, the first predetermined volume and the second predetermined volume may preferably be different.

There is even further provided in accordance with a preferred embodiment of the present invention, a set of at least a first and a second meal for use in making an evaluation of at least two causes of functional gastro-intestinal disorders in a single procedure the first meal comprising a first predetermined volume and having a first predetermined gastric retention characteristic, and the second liquid meal comprising a second predetermined volume and having a second predetermined gastric retention characteristic, wherein the second meal is administered to the subject after the first liquid meal has begun emptying from the stomach of the subject, and wherein the measured gastric emptying rates of the first and second meal are utilized to determine the gastric accommodation of the subject, such that an evaluation of at least two causes of functional gastro-intestinal disorders can be made in a single procedure.

Furthermore, in accordance with yet another preferred embodiment of the present invention, there is provided a set of at least one meal for use in making an evaluation of at least two causes of functional gastro-intestinal disorders in a single procedure, the at least one meal comprising a predetermined volume, and having a predetermined gastric retention characteristic, wherein at least two measurements of the gastric emptying rate of the at least one meal are performed as a function of the volume of the meal having exited the stomach of the subject, and wherein the at least two measurements are utilized to determine the gastric accommodation of the subject, such that an evaluation of at least two causes of functional gastrointestinal disorders can be made in a single procedure.

There is also provided in accordance with a further preferred embodiment of the present invention, a set of at least a first and a second meal for use in providing an indication of the visceral sensitivity of a subject, the first meal comprising a first predetermined volume and having a first predetermined gastric retention characteristic, and the second liquid meal comprising a second predetermined volume and having a second predetermined gastric retention characteristic, wherein the second meal is administered to the subject after the first liquid meal has begun emptying from the stomach of the subject, and wherein the measured gastric emptying rates of the first and second meal are utilized to determine the gastric accommodation of the subject, such that the gastric emptying and the gastric accommodation of the subject are known, and wherein information is provided by the subject about the level of dyspeptic symptoms perceived at least upon administration of the first meal and the second meal, the information being correlated with the gastric emptying and gastric accommodation of the subject by means of a gastrointestinal diagnostic processor, such that an output indicative of the visceral sensitivity of the subject is obtained.

In accordance with yet another preferred embodiment of the present invention, there is provided a set of at least one meal for use in providing an indication of the visceral sensitivity of a subject, the at least one meal comprising a predetermined volume, and having a predetermined gastric retention characteristic, wherein at least two measurements of the gastric emptying rate of the at least one meal are performed as a function of the volume of the meal having exited the stomach of the subject, and wherein the at least two measurements are utilized to determine the gastric accommodation of the subject, such that the gastric emptying and the gastric accommodation of the subject are known, and wherein dyspeptic symptoms of the subject are ascertained as a function of the volume of the meal retained in the stomach of the subject, the information being correlated with the gastric emptying and gastric accommodation of the subject by means of a gastro-intestinal diagnostic processor, such that an output indicative of the visceral sensitivity of the subject is obtained.

BRIEF DESCRIPTION OF THE DRAWINGS

The present invention will be understood and appreciated more fully from the following detailed description, taken in conjunction with the drawings in which:

in FIG. 4A are shown results for a subject with a normal gastric accommodation function, while in FIG. 4B are shown results for a subject with a gastric accommodation disorder;

in FIG. 5A, there is shown a block diagram of the component parts of a gastric accommodation test system, while in FIG. 5B are shown examples of the output data obtained from the data processor of such a system; FIG. 5C is a schematic illustration of a breath tester, constructed and operative according to yet another preferred embodiment the present invention, which is capable of providing multi-functional gastric diagnosis information to the physician, in addition to that related to gastric emptying and gastric accommodation; while FIG. 5D shows a schematic representation of a preferred display output screen of a system such as that in FIG. 5C;

FIG. 7 is a table showing the deviation of the gastric emptying parameters between a series of subjects, some showing abnormal gastric accommodation and some being asymptomatic for two-meal and two-test procedures;

FIGS. 9A and 9B show curves obtained from normal individuals after administration of low volume and high volume liquid test meals respectively, while FIG. 9C shows a curve obtained from a subject with impaired gastric accommodation;

FIGS. 10A and 10B show schematic samples of gastric emptying curves from symptomatic subjects for the second day test. In FIG. 10A, a 200 ml. high caloric test meal is administered and in FIG. 10B, an 800 ml. high caloric test meal is administered;

DETAILED DESCRIPTION OF PREFERRED EMBODIMENTS

Figure 1A:
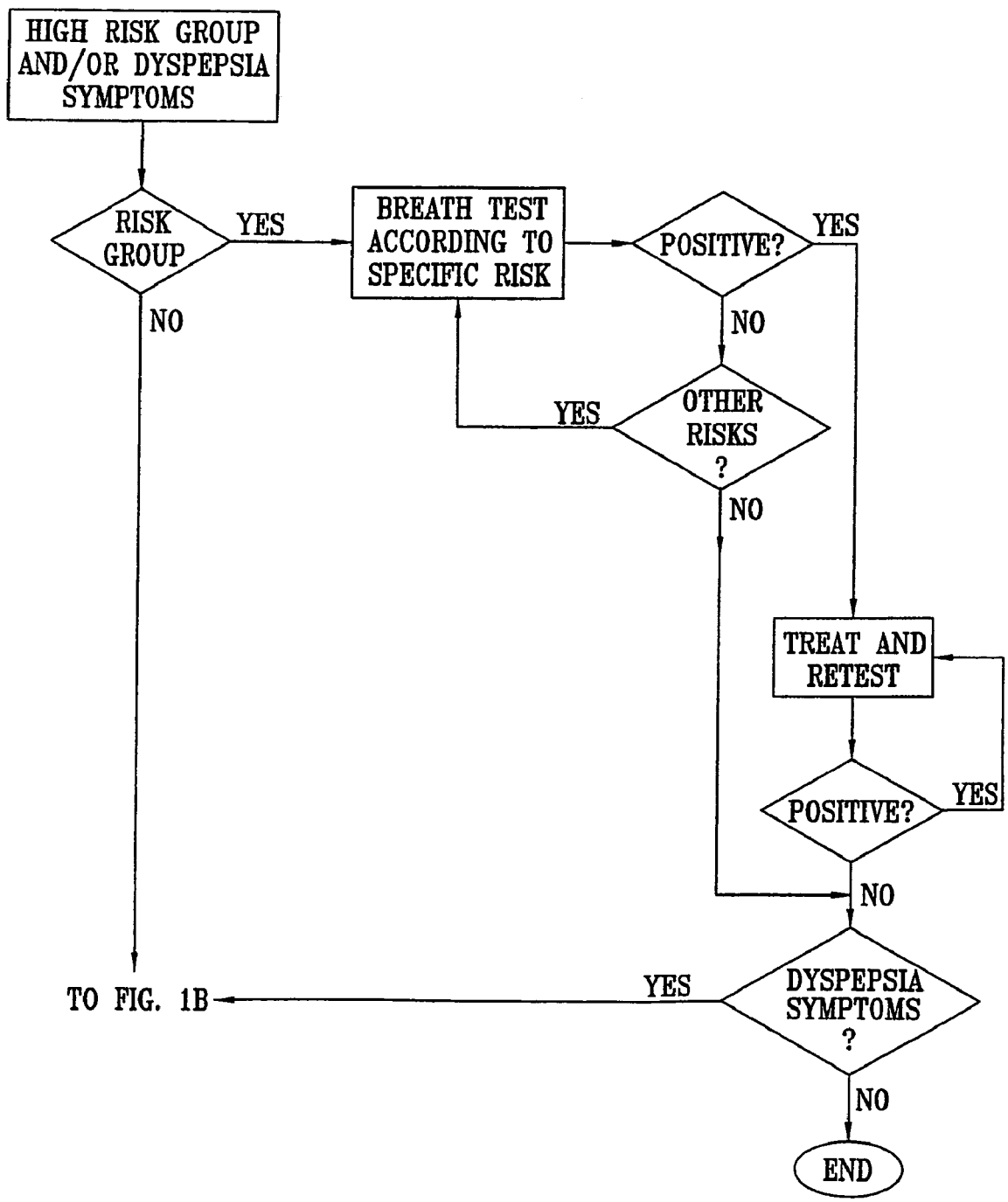
FIGS. 1A and 1B show schematic flow charts describing possible courses of detection and treatment for asymptomatic patients belonging to a GI high risk group (FIG. 1A), or for patients with symptoms of dyspepsia or IBS (FIG. 1B)
Figure 1B:
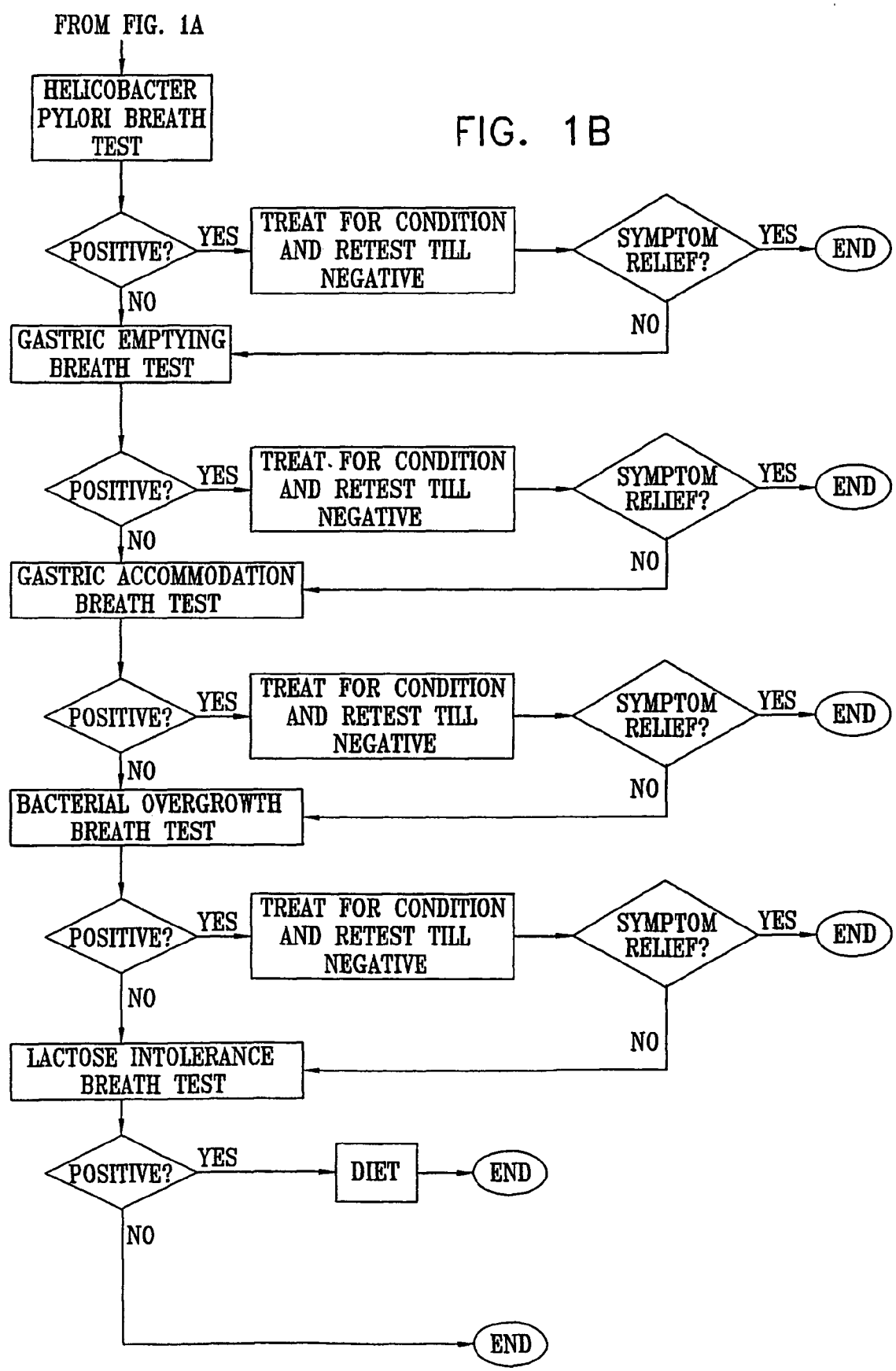

Reference is now made to FIGS. 1A and 1B, which illustrate schematically a flow chart describing possible courses of detection and treatment for patients with symptoms of dyspepsia or IBS, or asymptomatic patients belonging to a GI high risk group, as defined hereinabove. The flow chart is not intended to illustrate a definitive algorithm for a comprehensive diagnosis and treatment routine, but rather to illustrate some of the possible courses open to the treating physician, which can be taken using the methods and apparatus of the preferred embodiments of the present inventions. Though the tests in the preferred methods illustrated in FIGS. 1A and 1B are described as breath tests, it is to be understood that they can be equally well performed by other methods, as described hereinbelow.

Figure 1C:
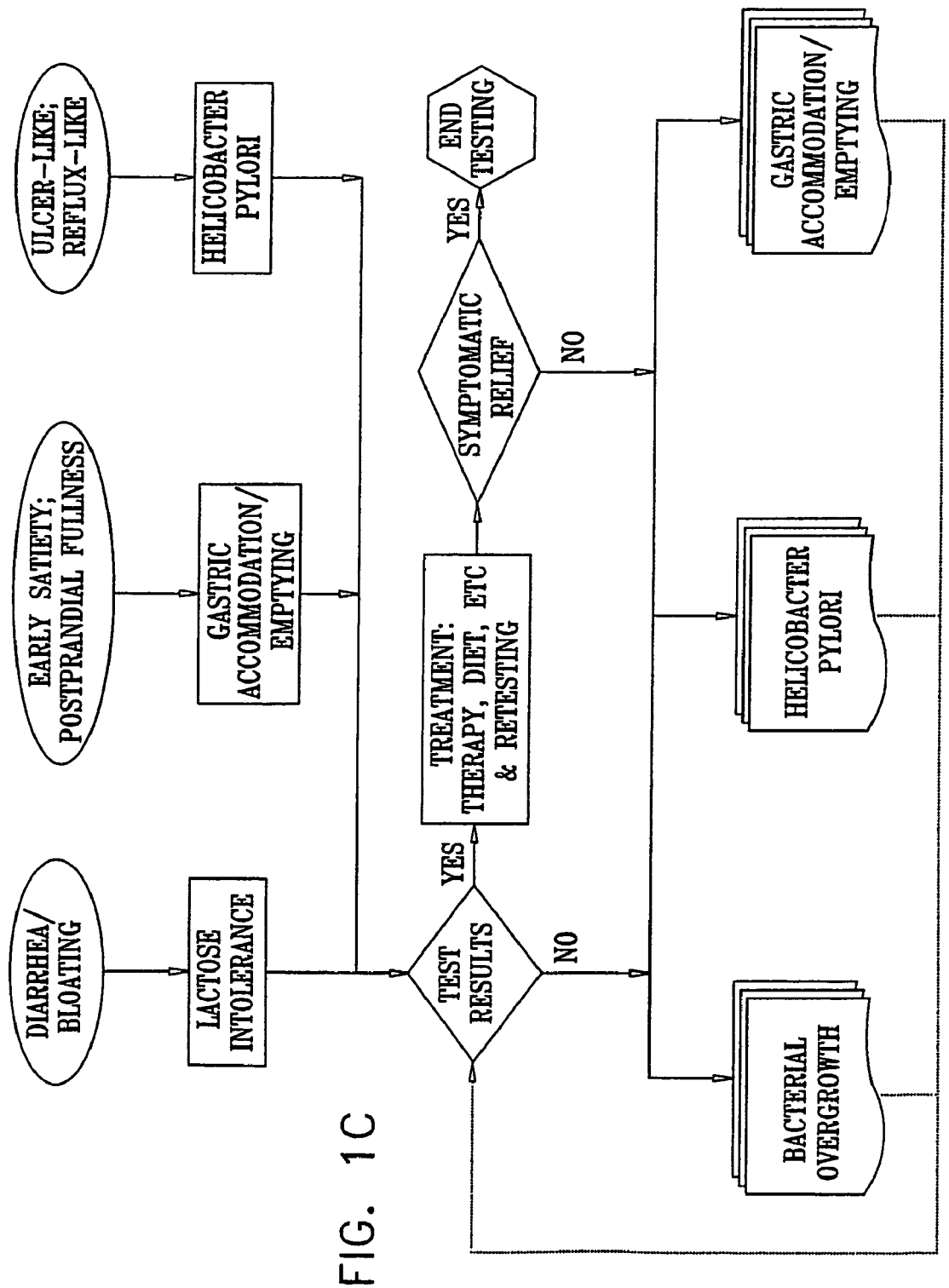
FIG. 1C is an alternative schematic diagram for illustrating a method of detection and treatment for patients suspected of having any of the above-mentioned GI problems, showing the proposed tests organized in a parallel arrangement.

Reference is also made to FIG. 1C, which is an alternative schematic diagram for illustrating a method of detection and treatment for patients suspected of having any of the above-mentioned GI problems. In the flow chart of FIG. 1C, the proposed tests are organized in a parallel arrangement, such that the physician can perform the required tests in the order of the intensity or the urgency of the patient's symptoms. Thus, for example, a subject suffering from gastric reflux would first be tested for H-p infection, and only if the test proved negative, or if the test were positive and the treatment did not provide symptomatic relief, would it be necessary to initiate another test other than that for H-p.

More detailed explanations are now presented of the methods of executing each of the tests shown in FIG. 1B, according to the methods and apparatus of preferred embodiments of the present invention. Though in each of the following sections, the tests are generally described in terms of the procedures for breath tests, this being a particularly convenient way of executing the tests, it is to be understood that they can be performed, where appropriate, by other methods and on other apparatus, as described hereinbelow. Use of such alternative methods or systems is particularly applicable to the gastric emptying test and the gastric accommodation tests, though the breath test may still be the method of choice.

1. Breath Test for *Helicobacter Pylori*

The breath test for *Helicobacter pylori* infection is well documented in U.S. Pat. No. 6,067,989 for "Breath Test for the Diagnosis of *Helicobacter pylori* in the Gastrointestinal Tract", assigned to the assignee of the present application, and herein incorporated by reference in its entirety, and no further details are therefore presented here of the test itself. The use and position of the test in the diagnostic hierarchy of FIG. 1B is described above, and below in relation to FIGS. 1C, 5C and 5D.

2. Gastric Emptying Breath Test (GEBT)

Symptoms related to delayed gastric emptying include nausea, vomiting and unstable glucose levels in diabetic patients. Poor emptying of the stomach can occur for several reasons:

1. The outlet to the stomach, including the pylorus and duodenum, may be obstructed by an ulcer or tumor or by a large and indigestible item that was swallowed.
2. The pyloric sphincter at the exit to the stomach may not open enough or at the right times to allow food to pass through. This sphincter is controlled by neurological reflexes to ensure that only very tiny particles leave the stomach and to limit the amount acid or food that can leave the stomach at one time to enter the small intestine. These reflexes depend on nerves which can sometime become damaged.
3. The normally rhythmic, 3-per-minute contractions of the lower part of the stomach can become disorganized so that the contents of the stomach are not pushed towards the pyloric sphincter. This also usually has a neuropathic origin; the most common cause is longstanding diabetes mellitus, but in many patients the cause of delayed gastric emptying is unknown, so the diagnosis is given as idiopathic gastroparesis.

Methods for the determination of gastric emptying of solids has been previously developed using radio-isotopically labeled carbon substrates, in the field of scintigraphy. In such methodology, the progress in the emptying of the labeled substrate from the stomach is followed, generally by direct imaging of the radiation emitted from the radioisotope. Breath tests for measuring similar time parameters have been proposed, in which the progress in the emptying of the labeled substrate from the stomach is followed by observing the labeled by-products of the substrate exhaled from the subject's breath, rather than by measuring what is left in the patient's body. Prior art gastric emptying breath tests (GEBT) commonly classify patients as normal, slightly delayed and delayed, according to the test protocol used.

Prior art GEBT's are generally performed by administering, in most of the cases, a solid test meal of 150-350 kilocalories, with a substrate labeled with either $C^{13}$ or $C^{14}$ as a marker. Examples of such substrates are Octanoic Acid, Sodium Octanoate, Sodium Acetate or Acyl Amino Acid as Acetyl Leucine, and others.

The optimal characteristics of these substrates are:
1. Good bonding to the test meal and so unreleased in the gastric environment;
2. Rapid release from the test meal when it leaves the stomach;
3. Immediate absorption, metabolization and conversion to measurable $CO_2$;
4. Dual usage for GEBT of liquids and solids for clinical simplicity; and
5. Easy preparation and reasonable cost.

Currently utilized substrates fulfill only some of these characteristics. Octanoic acid can be firmly bonded after cooking to the solid fats used in the meals. It is also quickly released from the food when passing through the duodenum, but after being absorbed in the small intestinal walls, it needs to be transported to the liver and metabolized there to produce $CO_2$. These processes are not directly related to the gastric emptying rate and can extend for a not insignificant time beyond the gastric emptying time, and are thus sources of delay in detecting the true gastric emptying rate. Furthermore, variability in the results may also be generated, since the $CO_2$ release is dependent on liver function, which may vary from subject to subject. Thus for example, it has been noted that even temporary impairment of liver function resulting from the consumption of a moderate quantity of alcohol can affect such prior art gastric emptying measurements for some time after the consumption, even though it would appear that the gastric emptying rate itself is probably unaffected by the previous alcohol consumption.

In addition, octanoic acid handling requires special equipment and meal preparation is unsuited and clumsy for performing in the clinical setting. Meal preparation outside the clinical setting, on the other hand, has the disadvantage that regulatory approval is required for the whole of the meal and for its manufacturing process, and not just for the labeled substrate, as is commonly accepted in most breath tests. Therefore, such a procedure requires a high level of standardization and its associated costs are high.

Sodium octanoate is the sodium salt of octanoic acid. It is easier to handle than the octanoic acid itself and is released from solids after leaving the stomach but it suffers from the same indirect metabolism path as octanoic acid, and is not easily mixed homogeneously with a solid meal.

Sodium acetate is generally considered the optimal substrate for the measurement of gastric emptying of liquids and semi-solids. This very simple and low cost substrate is rapidly metabolized after passing through the duodenum and readily converted into $CO_2$. However, it is easily diluted by water and acidic media, and in the gastric environment, is easily detached from its meal base, such that its progress does not necessarily reflect the emptying rate of the meal. Therefore it is clinically unpractical for use with solid meals. Furthermore, the need to bond it to a solid meal by industrial food preparation techniques gives it some of the disadvantages of octanoic acid.

Acyl Amino Acid as Acetyl Leucine has been recently proposed as an alternative GEBT substrate, and does not suffer from most of the technical drawbacks of the octanoates related to bonding, metabolization and versatility, but it is of higher cost. Furthermore, since it is not a naturally occurring substance, it may require a complex regulatory process before approval for use.

Sodium bicarbonate has also been proposed as an alternative substrate due to its being a readily accessible and abundant source of $CO_2$, and because of its simplicity and low cost. However, it too cannot be easily bonded to food, and releases its $CO_2$ content too readily through the gastric walls, making it impractical to use.

A breath test using an encapsulated version of $^{14}C$-labeled sodium bicarbonate was attempted by Zighelboim et al, as described in the article "Will a $NaH^{14}CO_3$ capsule method accurately measure gastric emptying?", published in Am. J. Gastroenterol. Vol. 88(3), pp. 462-4, March 1993. The test was unsuccessful, since the capsule used was bigger than the 2 mm size of the particles that the stomach evacuates as "liquid" food and was not bonded to the meal. Gamma camera measurements showed that it remained in the stomach after the food had emptied.

In performing a GEBT, one breath sample is usually taken as a baseline before administration of the meal, followed by breath samples during 4 hours usually taken every 15 min. The breath samples are analyzed by means of mass spectrometry, non dispersive infrared spectrometry, or any alternative method of isotopic analysis. The rate of metabolization of the substrate is determined from the change in $^{13}CO_2$ exhalation (delta over baseline—DoB) and the curve of the metabolized substrate excretion determined from the DoB as the Percentage Dose Rate (PDR) and expressed as:

$$y = at^b \exp(-ct) \quad (1)$$

wherein a, b and c are parameters to be fitted according to the measurement curve, such as by means of a least square fit, or by non-linear regression analysis.

A cumulative curve of the substrate excretion is then computed from the integral of the last curve as $$y_c = m(1 - \exp(-\kappa t))^\beta \quad (2)$$

and the parameters m, $\kappa$ and $\beta$ calculated by regression analysis. In order to derive these parameters an estimation of the $CO_2$ rate of production is derived from the DoB, based on the height and weight of the subject being tested. This normalized rate of production is known as the Percentage Dose Rate, PDR, and is more generally used than the DoB for Gastric Emptying applications. The total dose emitted is also a useful measure in analyzing the gastric emptying function, and is obtained by integrating the PDR values, and is known as the Cumulative Percentage Dose Rate, CPDR. The method of obtaining the PDR and CPDR from the subject's DoB, normalized according to the subject's weight and height, is disclosed by Y. F. Ghoos et al in "Measurement of gastric emptying rate of solids by means of a carbon-labeled octanoic acid breath test", published in Gastroenterology, Vol. 104(6), pp. 1640-7, June 1993.

There are three traditional parameters, derived from a GEBT, which describe the gastric emptying outcome of a patient.
1. The half emptying time ($t_{1/2}$) or the time in which half of the test meal has left the stomach, computed by setting $y_c = m/2$, such that $t_{1/2} = -1/\kappa * \ln(1 - 2^{-1/\beta})$.
2. The lag time ($t_{lag}$) defined as the time in which the emptying of solid phase of food begins after the initial liquid phase emptying, and given by $t_{lag} = (\ln \beta)/\kappa$.
3. The gastric emptying coefficient (GEC) equal to ln a. This parameter is related to the amplitude of the substrate recovery curve.

Preferred embodiments of the present invention relating to gastric emptying breath tests are now described. One of the advantages of the methods and apparatus of the present invention is the calculation and analysis of any of the above parameters in real time while measuring and determining when there is enough data to distinguish between patients with normal, slightly delayed and significantly delayed emptying. This therefore significantly shortens the time taken to achieve a definable result, from the four hours currently needed by prior art methods, such as using mass spectrometry measurements. Another significant advantage of the preferred embodiments of the methods and apparatus of the present invention is the possibility to follow changes in the dynamics of the gastric emptying, such as clearly identifying the peak or physiology noise in the emptying process. Suitable devices and methods for performing breath tests are described in the above-mentioned U.S. Pat. No. 6,186,958 for "Breath Test Analyzer"; in U.S. patent application Ser. No. 09/542,768 for "Breath test Methods and Apparatus", and in U.S. patent application Ser. No. 09/508, 805 for "Isotopic Gas Analyzer", all assigned to the assignee of the present application, and all incorporated herein by reference in their entirety. A breath test apparatus, according to a preferred embodiment of the present invention, for use in performing these tests for gastric emptying, is described below in connection with FIG. 2E.

There are 3 stages in this procedure:
1. Determining normal and abnormal values, or ranges of values, of $t_{1/2}$, $t_{lag}$, Delta over baseline (DoB) curve amplitude, and Gastric Emptying Coefficient (GEC) parameters by accumulating data from many test subjects.
2. Testing a subject and monitoring, in real time, the calculated $t_{1/2}$, $t_{lag}$, amplitude of DoB, and Gastric Emptying Coefficient (GEC), as the measurement proceeds.
3. Following the monitored graphs of these 4 parameters as they progress during the measurement, and determining by means of extrapolation at the earliest possible moment, a final estimated value, within the allowed error limits, at which it can be determined if one of the 4 parameters ($t_{1/2}$, $t_{lag}$, DoB or GEC) is abnormal, or if they are all normal. The error allowed can be a function of the estimated value obtained. When values are far from the border between the normal or abnormal ranges, larger errors can be tolerated than when borderline values are obtained.

As an example of the execution of this preferred procedure, table 1 shows the results of testing a single subject four times by administering 100 mg. of $^{13}$C-labeled octanoic acid and Acetyl Leucin as markers with a solid test meal of 150-350 kilocalories. The table shows the times after the peak when each of the 4 parameters were extrapolated to within 85% and 70% of their final asymptotic converged values.

There are cases of subjects with rapid gastric emptying, in whom a high DoB amplitude may be obtained even before the peak is reached, as determined by comparison with the typical time taken to reach the peak and the DoB levels reached in a normal subject.

Reference is now made to FIGS. 2A to 2D, which are a set of four graphs showing an example of the real time progress of the calculated $t_{1/2}$ (FIG. 2A), $t_{lag}$ (FIG. 2B), integrated marker exhalation as obtained from the area under the DoB curve (FIG. 2C), and GEC (FIG. 2D) of a chosen subject, as a function of time in hours. The results were taken using a breath test apparatus shown schematically in FIG. 2E, constructed and operative according to a preferred embodiment of the present invention. The breath is collected and its isotopically labeled content analyzed preferably according to the methods shown in the breath testers described in the above-mentioned patent documents. Curve fitting of the measured points to plots of the four gastric emptying parameters are preferably performed by means of a curve fitting algorithm, such as the Levenberg-Marquat algorithm and using the Lab View program, supplied by National Instruments Corporation, of Austin, Tex. 78759, U.S.A., which is built into the data processor of the breath analyzer, which is shown in the preferred embodiment of FIG. 2E within the dashed lines. Initial guess values for the previously described coefficients a, b and c, are derived from the expected values of $t_{1/2}$, $t_{lag}$ and GEC obtained from previous tests performed on the subject, or from an average of the normal ranges of these parameters from a large number of previously measured normal subjects, as stored in a database module of the data processor. The values of these parameters are continuously extracted from the calculated curves derived from the measured breathes, and compared repetitively with the stored norm values in the differential gastric emptying parameter comparison module. By this method of real time measurement and almost continuous checking of the measured curved for convergence to an asymptotic end value, the expected values of the gastric coefficients can be anticipated to good accuracy well before the asymptotic end point of the curve has been reached. A definitive result can thus be generated by this apparatus significantly more quickly than by prior art apparatus which does not provide real-time results of the breath test. In the example shown, extrapolation may be performed for the four gastric emptying parameters after approximately 1 hour, which is significantly faster than would be possible using prior art apparatus.

It is to be understood that the meaning of terms such as "virtually continuously", or "in real time", when used in connection with breath sampling, is dependent on the test concerned. Thus, for a test lasting only a few minutes, the terms may really mean non-stop sampling. On the other

TABLE 1

Estimated Time After Peak Necessary to Reach 85% & 70% Accuracy of GEBT Parameters (with extrapolation) for a Single Subject

| Test # | Time to peak (hours) | $t_{1/2}$ 85% | $t_{1/2}$ 70% | $t_{lag}$ 85% | $t_{lag}$ 70% | GEC 85% | GEC 70% | DoB Amplitude |
|---|---|---|---|---|---|---|---|---|
| 1 | 1.3 | 0.5 | 0.5 | 0.5 | 0.5 | 0.2 | 0.1 | immediate |
| 2 | 1 | 0.8 | 0.6 | 0.6 | 0.4 | 0.3 | 0.1 | immediate |
| 3 | 1 | 1 | immediate | 1 | immediate | 0.3 | 0.2 | immediate |
| 4 | 1.3 | 0.7 | 0.3 | 0.7 | immediate | 0.1 | immediate | immediate | hand, for tests such as gastric functioning tests which may last an hour or even more, samples taken periodically such as only every 10 to 15 minutes, for instance, would still be regarded in the art as being "virtually continuously" sampled, and measured in "real time", and are so described and claimed in this application.

Because there is sometimes no correlation between symptoms and delayed gastric emptying, the GEBT as described above is especially useful in the periodic management of diabetic patients for insulin/drug-food management as discussed in Gastric emptying in diabetes: clinical significance and treatment. Diabet Med., Vol. 19(3), pp. 177-194, March 2002. In the case of dyspepsia, dyspeptic symptoms are the main reason to test patients. It has been shown in the article by Maes BD, et al., entitled "Gastric emptying rate of solids in patients with nonulcer dyspepsia" published in Dig. Dis. Sci., Vol. 42(6), pp. 1158-62, June 1997, that delayed gastric emptying is not necessarily the origin of all dyspeptic symptoms, though first generation drugs for the treatment of gastric emptying, such as Cisparide or Erythromycin, generally help to reduce dyspeptic symptoms. The effectiveness of new emerging medicines, such as the newly proposed Tegaserod, in relieving these symptoms is not clear enough yet, but since such drugs were designed to be more GI disorder specific than those previously mentioned, diagnostic may be recommended before the drug is prescribed. This is especially important due to the fact that these drugs apparently treat the GI condition but do not cure it, and have to be administered continually to treat the disorder.

Other gastric motility disorders, related with visceral perception of pain, early fullness and bloating, include manifestations of impaired gastric distention and accommodation, for which the proper treatment includes the administration of drugs to relax the muscular tone, such as Glyceryl Trinitrate, serotonigenic agents or some antidepressants. Currently barostat studies are the only clinical method in clinical use to measure these disorders.

According to the preferred embodiments of the present invention, there is also provided a noninvasive, accurate and convenient method for the measurement of the severity of these gastrointestinal conditions related to gastric emptying and other gastric motility disorders.

In addition, according to more preferred embodiments of the present invention, there is also provided a substrate for isotopic breath tests that overcomes the disadvantages of the present available substrates. The substrate utilizes micro-encapsulated or an enteric coated isotopically labeled material. The coating can preferably be an enteric coating that is broken down in the duodenum or the small intestine, rather than in the stomach, due to the higher pH in those parts of the GI tract, typically 6, compared with that in the stomach, typically 2.5 to 3.5. Alternatively and preferably, a coating broken down by specific enzymes found only in the desired part of the GI tract can be used.

These capsules are preferably filled with $^{13}$C-labeled substrate of the simplest materials, such as sodium bicarbonate or sodium acetate. Micro-encapsulation thus allows specific marker drug release of such materials along the duodenum in a rapid and homogenous way, only after emptying of the meal from the stomach.

Substrates such as octanoic acid are usually incorporated into egg yolk and an omelet is prepared therefrom as the test meal. It is know that micro encapsulation is produced during the meal cooking, since oils from the egg yolk form a hydrophobic coating around the octanoic acid and protect it during the cooking process, providing its good bonding characteristics to the meal.

As previously mentioned, according to another preferred embodiment of the present invention, micro-encapsulation can be used wherein the coating is decomposed by means of a selected enzymatic, rather than pH environment. The selectivity in this method relies on the presence of specific enzymes in the duodenum, such as those secreted by the pancreas or through. the bile ducts. The advantages of this preferred embodiment are that it can be used for the micro-encapsulation for liquid meals, and also is not dependent on the variability of pH between subjects.

These preferred micro-encapsulated substrates have a number of advantages over prior art substrates, as follows:
1) Enablement of real time analysis of gastric emptying, since the micro-capsules are homogeneously distributed in ingested food.
2) Specific release of the substrate material, such as sodium acetate or bicarbonate, in the duodenum or small intestine or colon, in a rapid and homogeneous way, only after emptying from the stomach. The release can be made pH dependent or specific enzyme dependent. Furthermore, the absorption of the substrate can be achieved without the need of an additional metabolic step.
3) Possibility of using the same material for both solid and liquid meals, since the bonding properties to food, the stability within the gastric environment, the taste, the convenience of use, etc., are independent of the material itself, and dependent only on the properties of the chosen micro-encapsulation coating.
4) Enablement of the use of low cost $^{13}$C markers, while micro-encapsulation itself is a reasonably low cost process, costing in the region of tens to one hundred dollars per kilogram.

3. Test for Gastric Accommodation (GA Test)

An upper stomach with proper accommodation characteristics allows it to maintain constant pressure while the volume increases. This part of the stomach is responsible for gastric emptying of liquids and has almost no effect on gastric emptying of solids. The lower part of the stomach is not thought to have a significant effect on gastric emptying of liquids. In addition it is known from the literature that excess intra-gastric pressure is related to upper gastrointestinal symptoms and that inhibition of gastric emptying is required when high calorie meals are administered.

There is therefore provided, according to yet more preferred embodiments of the present invention, gastric accommodation tests (GAT) and apparatus for performing these tests, based on the principle that for different distension volumes, the gastric emptying rate of liquids is unaffected in normal individuals, but is impaired for patients with impaired accommodation.

Two methods for performing these GAT's are proposed, according to different preferred embodiments of the present invention. As previously mentioned, these tests are primarily described in their breath test embodiment forms.

A. The Two Meal Method

A low volume, preferably of the order of 100 ml to 350 ml, of a liquid meal preferably containing a $^{13}$C-labeled substrate is administered to the subject, in a similar manner to that known in prior art gastric liquid emptying breath tests, such as described by Mossi et al., in Digestive Diseases and Sciences, Vol. 39, No. 12, December 1994, Suppl., pp. 107S-109S, incorporated herein by reference. A suitable $^{13}$C-labeled substrate may comprise, but is not limited to, octanoic acid, sodium acetate, glucose, sodium octanoate, acetyl-leucine, Spirulina algae, micro-encapsulated bicarbonate or another substrate, preferably undergoing direct and fast metabolism, which can be utilized for the measurement of the liquid gastric emptying rate. The isotopic ratio in the exhaled breath is measured at baseline and thereafter at regular intervals in real time. A Delta over Baseline curve is preferably traced and a curve of the rate of liquid emptying or emptying from the stomach is determined from the outcome. A typical DoB curve as a function of time, resulting from this procedure is shown on the left hand part of FIG. 4A, and this is the typical shape of a normal gastric accommodation curve.

According to a first method of these preferred embodiments of the present invention, a second liquid meal, preferably comprising at least one of:
1) a high volume of water, typically from the order of 500 ml to 1.5 liter, or more;
2) an isotonic solution;
3) an acidic solution, such as one having a pH of 2.5 or lower; or
4) a caloric liquid meal; is administered to the subject to induce gastric distention, and/or to limit the rate of gastric emptying. This second meal is administered at time $T_o$ as soon as enough data has been accumulated from the first curve to evaluate the gastric emptying rate of the first meal to the required accuracy, as described hereinabove in the section on the breath test for gastric emptying rate. $T_0$ is shown on the curve in FIG. 4A, and in those figures thereafter where $T_0$ is indicated. The change in slope on the emptying curve, or the change in the gastric emptying parameters, such as $t_{1/2}$ or $t_{lag}$, is derived from the DoB plot. The desirable characteristics of such a second liquid meal are at least one of:
1) having the effect of causing a distension effect in the proximal stomach, or
2) having a high caloric value or low pH value, so that inhibition of gastric emptying is required to avoid overloading of the small intestine.

Therefore, one preferred and desired approach is to administer the same liquid test meal as was administered in the first meal but with a large amount of water, so as to induce stress of the fundus, and thus to measure the emptying rate of meals of similar caloric content but with different volumes. According to different preferred embodiments, this second meal can be either with or without an isotope labeled substrate. If no isotope labeled substrate is used in this second meal, the effect of gastric accommodation of the first meal is determined by means of the effect of the increased volume of the second meal on the first emptying curve, if such an effect is present. In this case, it is important that the second meal be a low natural $^{13}C$ source, so that it does not interfere with the $^{13}CO_2$ levels generated from the metabolized $^{13}C$-labeled substrate used in the first meal.

Figure 3:
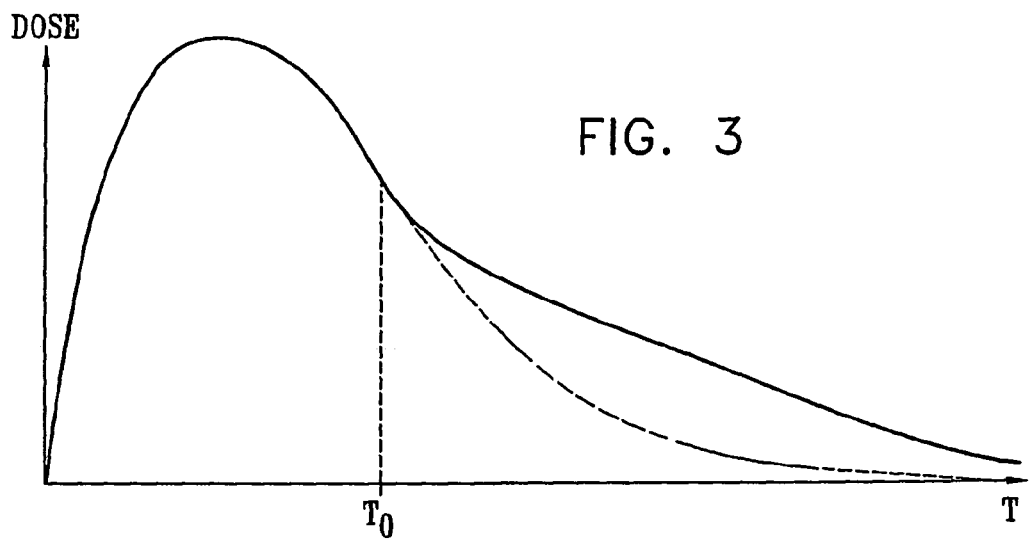
FIG. 3 is a schematic drawing of a curve of the DoB or of the exhaled dose of labeled decomposition product obtained in a GEBT performed with an unlabelled second meal.

This effect is shown by reference to FIG. 3, which is a schematic drawing of a curve of the DoB or of the exhaled dose of labeled decomposition product obtained in a GEBT performed with an unlabelled second meal. At the time $T_0$, at which time the gastric emptying parameters have been determined with sufficient accuracy, the second meal is administrated. The extrapolated shape of the curve beyond time $T_0$, which would have been obtained without the administration of the second meal, is shown as a dotted line. The values of gastric emptying parameters obtained from this curve are recorded as soon as available, i.e. close to or immediately after time $T_0$. Administration of the second meal may result in a change in the asymptotic tail end of the curve, as shown by the solid line. New values of gastric emptying parameters are now calculated for this new curve, and the values compared with the gastric emptying parameters originally obtained from the initially obtained curve. In a normal subject, the values of gastric emptying parameters will be little changed, if at all, while a subject with impaired gastric accommodation will generally show noticeably changed values. In general, for the two meal tests, the level of gastric accommodation impairment is defined by the detection of clinically significant differences between corresponding sets of gastric emptying parameters obtained from administration of the two meals. The extent of such differences enable the detected gastric accommodation to be categorized as normal, abnormal or borderline.

Figure 4A:
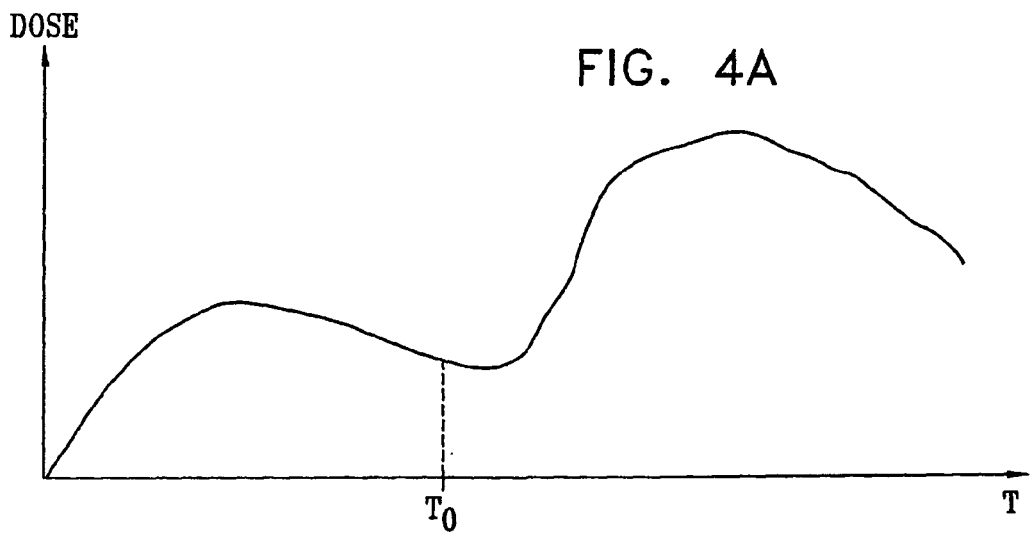
FIGS. 4A and 4B are typical DoB curves as a function of time, resulting from the two meal procedure.

In the case of an isotopically labeled second meal, the preferred procedure is simpler and more direct, since a new curve can be modeled directly for the second meal and a new set of gastric emptying parameters is calculated to determine the emptying rate of the second meal directly, as explained hereinbelow in connection with FIG. 4A and following. The effects of the second meal on the emptying curve depend upon the composition of the meal. In a normal subject, the second liquid meal does not generally significantly affect the shape of the second emptying curve, which has a normal shape, similar to that of the first meal, as shown by the similarity of the two curves shown in FIG. 4A. The first meal shown in the example plotted in FIG. 4A was of 200 ml. of Ensure Plus®, with 100 mg. of $^{13}C$-sodium acetate added thereto. The second meal was 200 ml. of Ensure Plus® with 600 ml. of additional water, and 100 mg. of $^{13}C$-sodium acetate added thereto. The quantity of labeled isotope added to the meals of the various preferred embodiments of the present invention are all given as 100 mg., though it is to be understood that this quantity could be varied according to the type of test, the subject or the type of meal.

Figure 4B:
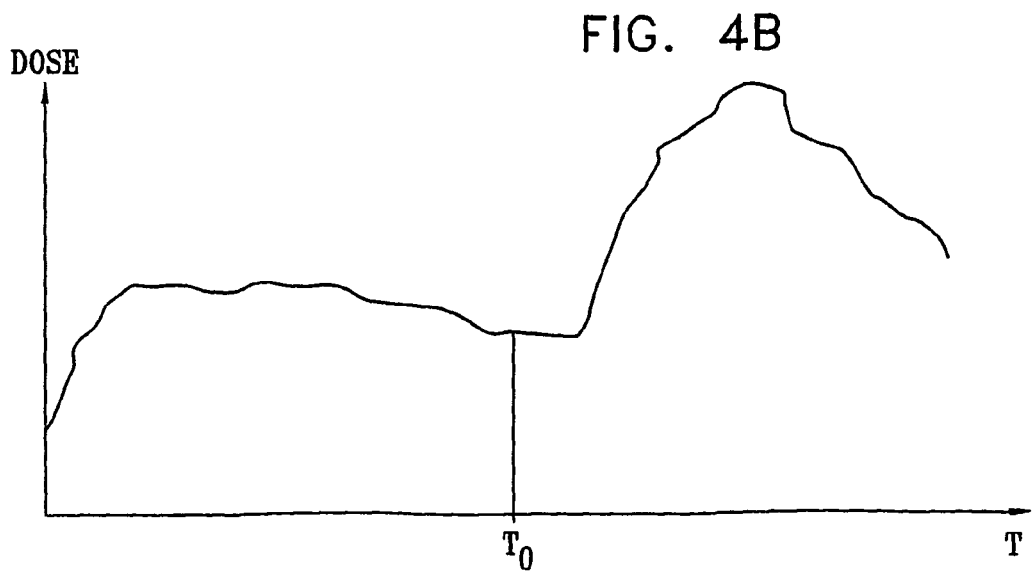

On the other hand, in subjects with some forms of gastric accommodation disorder, a possible outcome of the breath test conducted according to this preferred embodiment, would be to change the shape of the emptying curve on administration of the second meal, as typically shown in FIG. 4B. In the example brought in FIG. 4B, using the same meals as those used in the test illustrated in FIG. 4A, it is observed that the gastric emptying is significantly quicker for the second meal than for the first. For the subject tested in FIG. 4B, for instance, $t_{1/2}$ was found to be 174 minutes for the first meal (200 ml) and only 112 minutes for the second, high volume meal (800 ml), thus showing that the subject has a significant gastric accommodation anomaly.

Figure 5A:
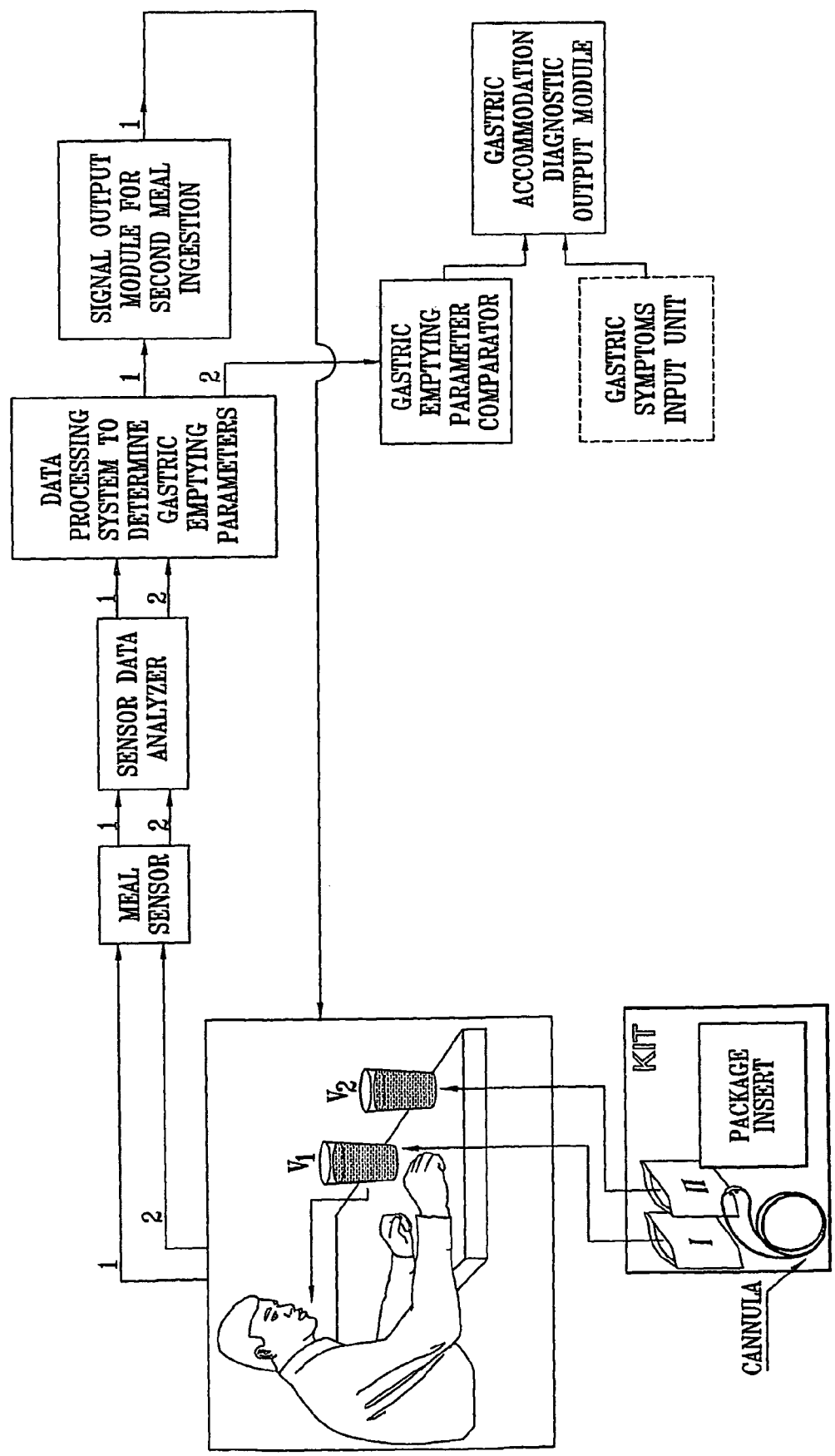
FIGS. 5A to 5D, schematically illustrate systems, according to more preferred embodiments of the present invention, for performing gastric functioning tests, and especially gastric accommodation tests.
Figure 5B:
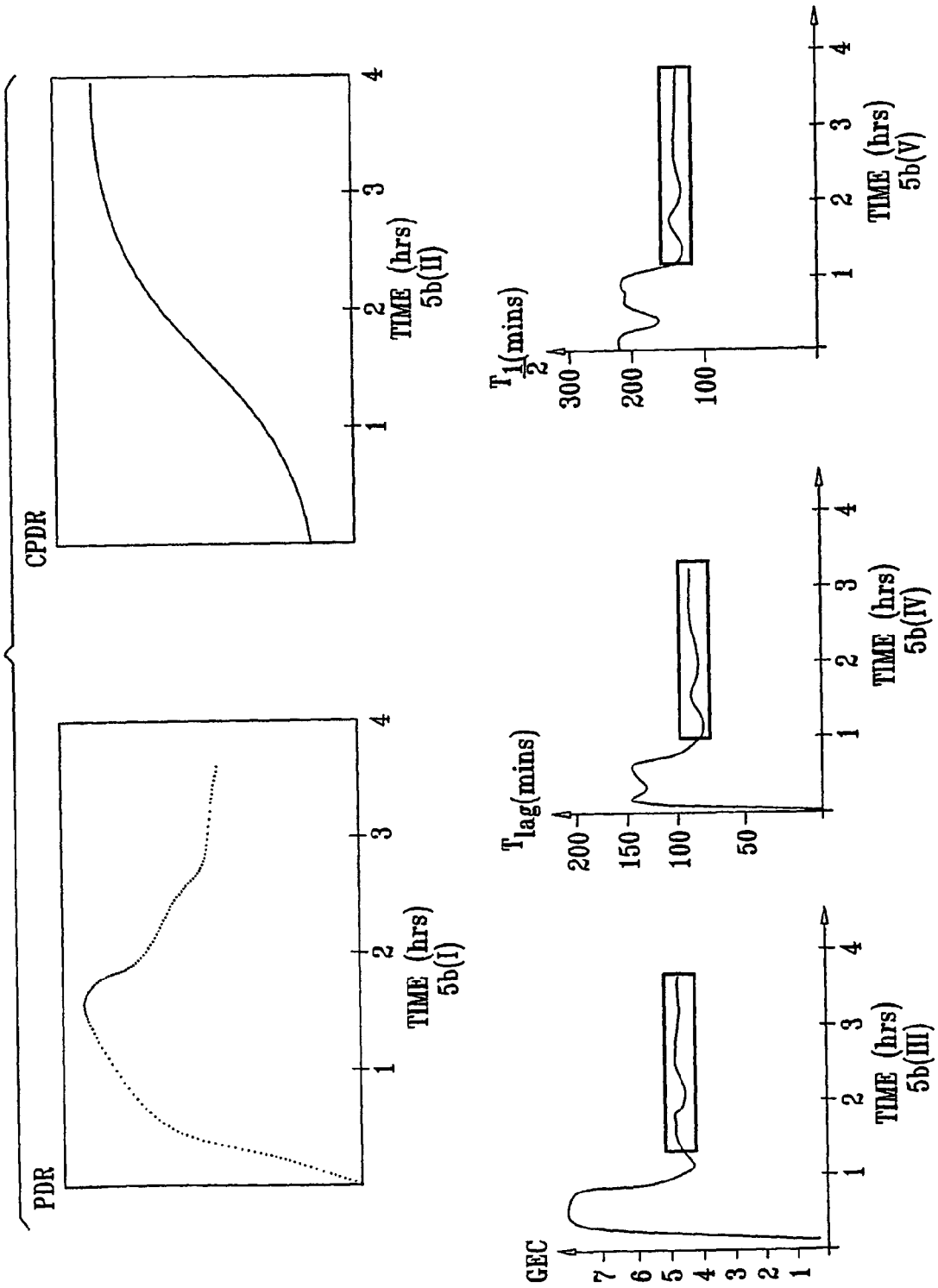

Reference is now made to FIGS. 5A and 5B. FIG. 5A a schematic representation of a system, according to another preferred embodiment of the present invention, for performing the gastric accommodation tests as described in the test methods above, and in FIG. 5B, are shown examples of the output data obtained from the data processor of such a system, from which may be obtained indications of the presence or absence of gastric accommodation problems in the subject.

Referring first to FIG. 5A, there is shown at the input, a meal sensor, which senses the test meal on leaving the stomach of the subject, and provides a measure of the fraction of the marker (i.e. the test meal) expelled from the stomach or remained it the stomach as a function of time elapsed from administration of the first test meal V1. This sensor may preferably be a breath test measurement relating to the PDR of the marker in the test meal on leaving the stomach, or any other sensor which is capable of plotting the progress of the marker from the stomach, such as MRI, scintigraphy (gamma imaging), CT, X-ray, ultrasound, or even such simple measurements as external volumetric measurements of the subject's abdomen to determine volume reduction of the stomach region.

The signal from the gastric emptying meal sensor is then preferably passed to a meal sensor data analyzer, which analyzes the meal sensor data output and provides the necessary information concerning the percentage meal expulsion from the subject's stomach as a function of elapsed time, for further processing by the system. For a preferred embodiment in which the meal sensor is a breath test sensor, such a data analyzer could be a PDR curve generator, which takes into account the subject's height and weight. At the same time, for a breath test application, the data analyzer could also continuously calculate the integral under this curve and a CPDR plot against time is provided. In FIG. 5B, the intermediate results of these two plots are shown in the top two graphs, designated 5B(i) and 5B(ii), which are generated by the meal sensor data analyzer.

Figure 2A:
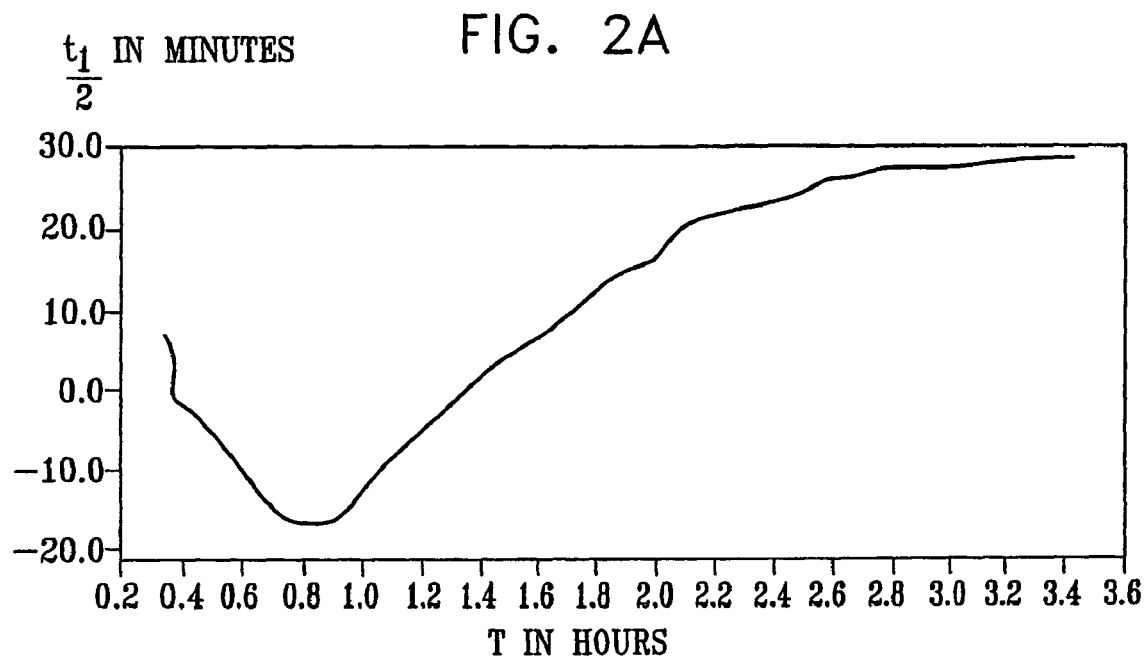
FIG. 2A to 2D are a set of four graphs showing an example of the real time progress of the calculated $t_{1/2}$, $t_{lag}$, DoB and GEC gastric emptying parameters of a subject, as a function of time in hours.
Figure 2B:
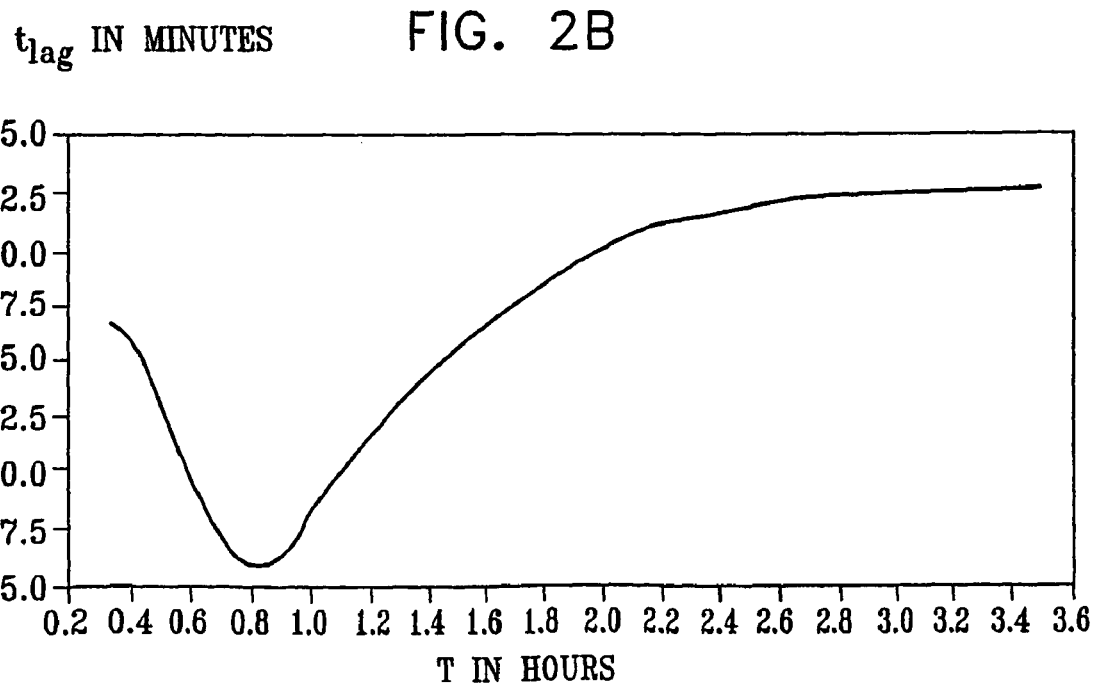
Figure 2C:
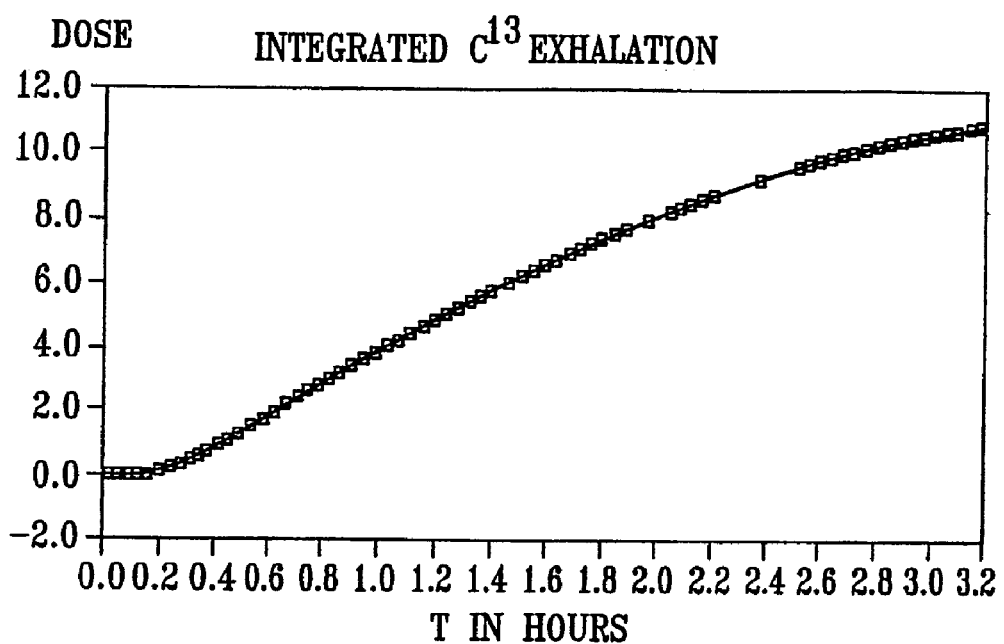
Figure 2D:
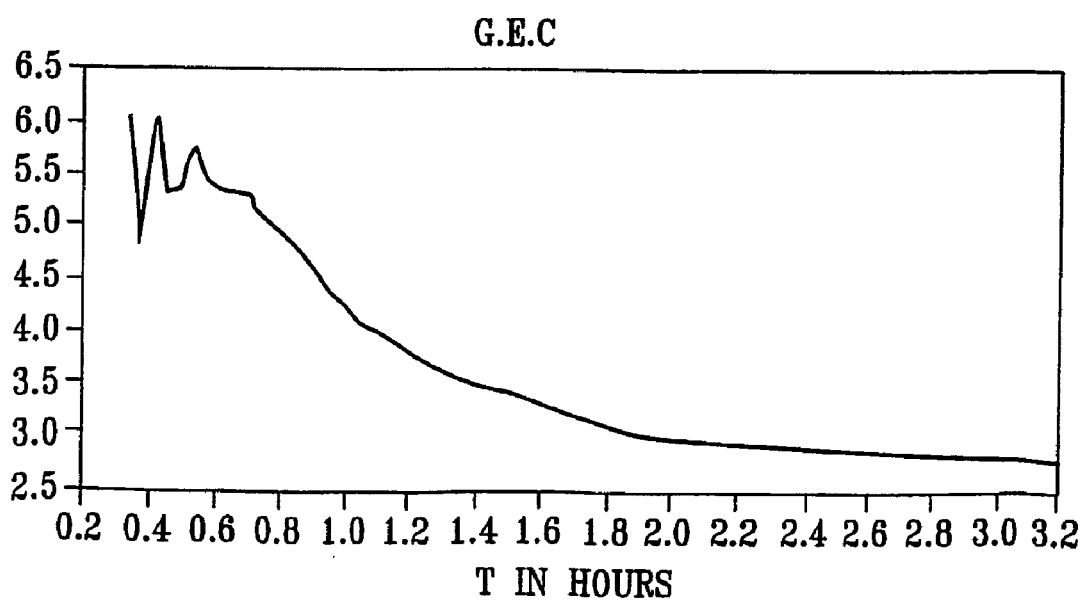
Figure 2E:
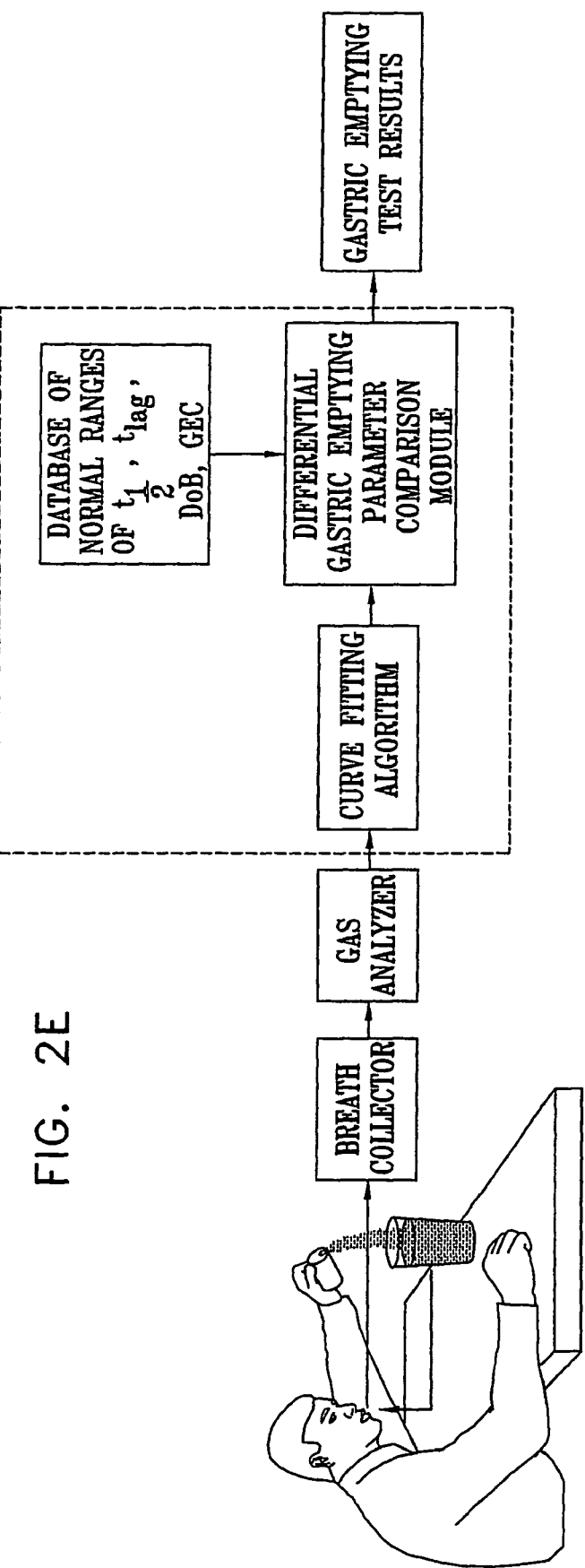
FIG. 2E is a schematic representation of a preferred breath test apparatus, for obtaining and using this data to determine the normalcy of these parameters in a subject.

Returning now to FIG. 5A, the analyzed data is now processed by the data processing system, which may, for a breath test preferred embodiment of this invention, be similar to that shown within the dashed lines in the representation of the gastric emptying tester of FIG. 2E. The curve fitting module of the data processing system repeatedly attempts to obtain values of the parameters a, b and c of equation (1) above from the curves of the PDR or the DoB, and from the curves of the CPDR, or alternatively the integrated DoB, attempts are made to obtain values of m, κ and β of equation (2) above. Once convergent values of these parameters have been obtained, from the value of m, the parameter $t_{1/2}$ is computed, by setting $y_c=m/2$, as described above, and from the value of the parameter a, the value of the GEC, equal to log a, is obtainable. The value of $t_{lag}$ is derived from $t_{lag}=(\ln \beta)/\kappa$ and can be evaluated from the position of the peak of the curve after administration of the meal, as well. Other parameters which the data processing system may generate for use in assessing the test results, are the integral area under the PDR or DoB curves, indicating the total dose detected, and the amplitude of the PDR or DoB curves.

It should be noted that since the gastric accommodation test is performed on the same subject utilizing two consecutive meals with similar amounts of labeling material, the PDR curve can be replaced by a DoB curve for simplification. In this case the GEC does not reflect the actual GEC of the subject, and the actual CPDR is not computed. This variance does not affect the outcome of the test because only the variation between parameters is computed for test results on the same patient, and not the parameters themselves as explained below. Other parameters such as $t_{1/2}$, $t_{lag}$, the DoB amplitude and integral under DoB curve are unaffected by this simplification.

In the bottom half of FIG. 5B, there are shown typical time plots obtained from the output of the curve-fitting algorithm module of the data processor, in which the calculated values of the gastric emptying parameters GEC, $t_{lag}$ and $t_{1/2}$ are shown as a function of elapsed time. These graphs are designated 5(iii), 5(iv) and 5(v) respectively. In each of the graphs, it is seen how the measured parameter converges with elapsed time to its final determined value. During the final stages of convergence, the system is able retroactively to define an error band around the finally asymptotic end-value, and the processor is preferably programmed to recognize this error band from the converging behavior of the curve. The width of the error band may preferably be determined according to the result being obtained in real time. When it is apparent from the value of the parameter being plotted that the final value is either clearly out of range of the norm, indicating clearly impaired gastric emptying, or well within the normal range, a wide error band is used, enabling the decision point about terminating that segment of the test to be reached sooner. On the other hand, if the parameter seems to be on the border line between normal and abnormal values, a narrow error band is used in order to increase the final accuracy attainable for that parameter.

Referring back now to the system of FIG. 5A, as soon as one, or according to another preferred embodiment, more than one of the parameters is detected as being confirmed as having entered the final error band, the system provides an output signal, either to the subject or to attendant medical staff, informing that the second meal of the gastric accommodation test should be taken by the subject. The system preferably continues for a limited time to plot and calculate the gastric emptying parameters of the first meal, in order to increase the accuracy of the values finally generated, since it takes some time before the effects of the second meal begin to appear at the meal sensor. This is particularly so when a breath test sensor is used, whereby commencement of detection of the second meal generally begins only when the meal begins to exit the stomach, or even some time thereafter because of the metabolic path delay time.

Once the second meal has been ingested, the gastric accommodation system plots the progress of the second meal, in a similar way to which it measured that of the first meal, and a second set of gastric emptying parameters are generated by the system, as shown in the bottom half of FIG. 5A. However, the data processing system must utilize the extrapolated values of the PDR or DoB curve of the first meal for subtracting from the PDR or DoB values of the second meal, as will be explained hereinbelow in connection with FIG. 6.

Finally, once the data processor has determined that the second meal gastric emptying parameters have been obtained with sufficient accuracy, the system preferably compares corresponding sets of parameters from the two meals, and according to predetermined criteria, provides a diagnostic output about the presence or absence of impaired gastric accommodation of the subject. According to one preferred criterion, the gastric accommodation is defined as being impaired if the value of $t_{1/2}$ for the second meal is at least 10% less than that of the first meal, or if the value of GEC for the second meal is at least 5% more than that of the first meal. Other preferred criteria relating to the difference between the values of the amplitude of the peak of the PDR curve or of the DoB curve for the two meals, may also be preferentially used, with an increase of more than 10% between the first meal and the second being considered as indicating impaired gastric accommodation. Alternatively and preferably, the integral areas under the PDR (i.e. CPDR) or the DoB curves can be the parameters used, with a 10% increase being defined as being indicative of impaired gastric accommodation.

According to further preferred embodiments of the present invention, combinations of parameters may be used for constructing the diagnostic criterion, such that if a predefined number of the given parameters indicate impaired accommodation, then this is regarded as being sufficient to make the diagnosis, even if other of the parameters do not show significant differences. Furthermore, different parameters in the combination used for the diagnostic criterion may be given different weightings, such that those parameters which are more critical or indicative of the subject's gastric status are given more weight. For example, the half time may be given a higher weighting than the CPDR, thereby implementing an expert system into the apparatus capable of providing higher sensitivity and specificity to the procedure.

Figure 5C:
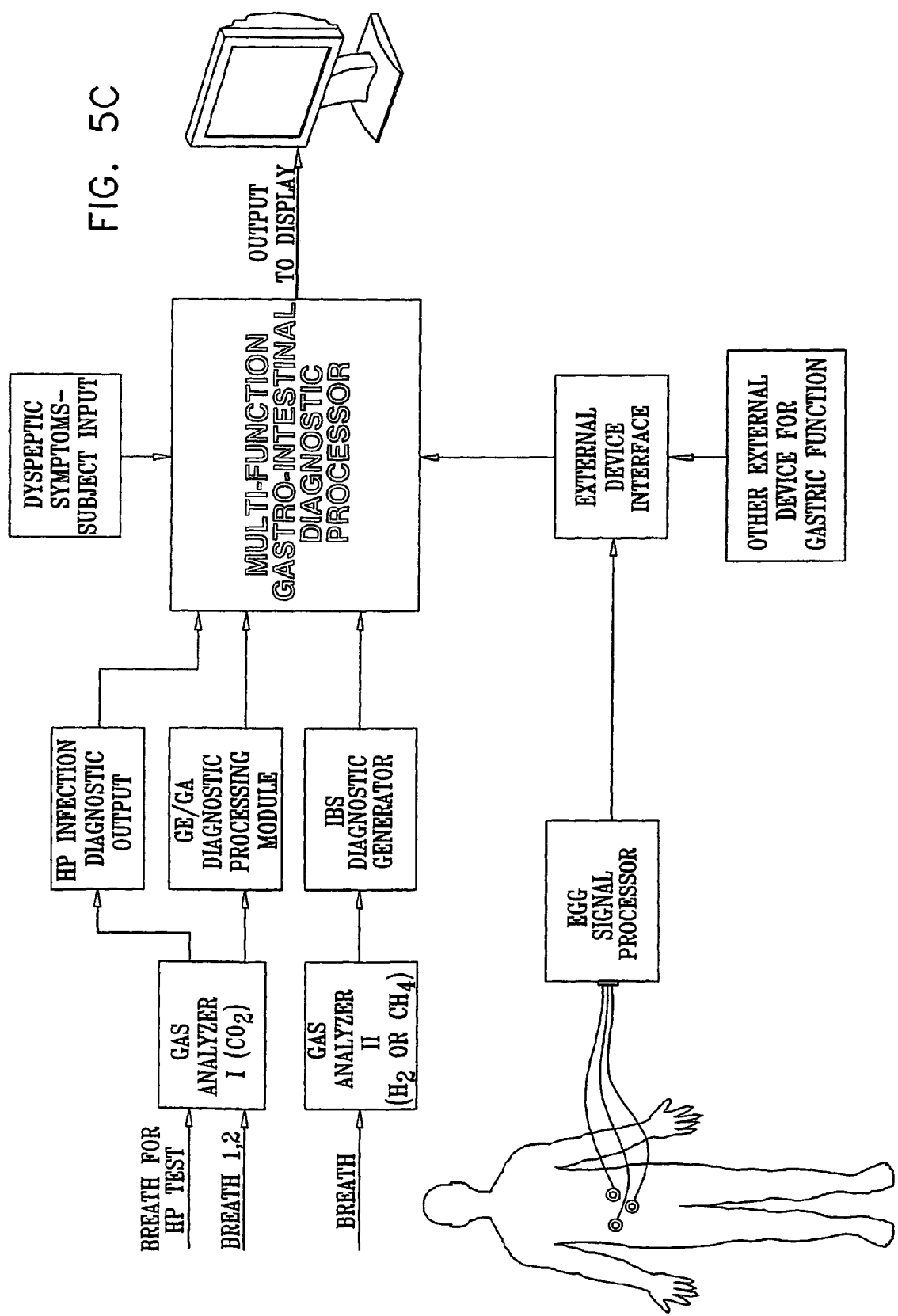
Figure 5D:
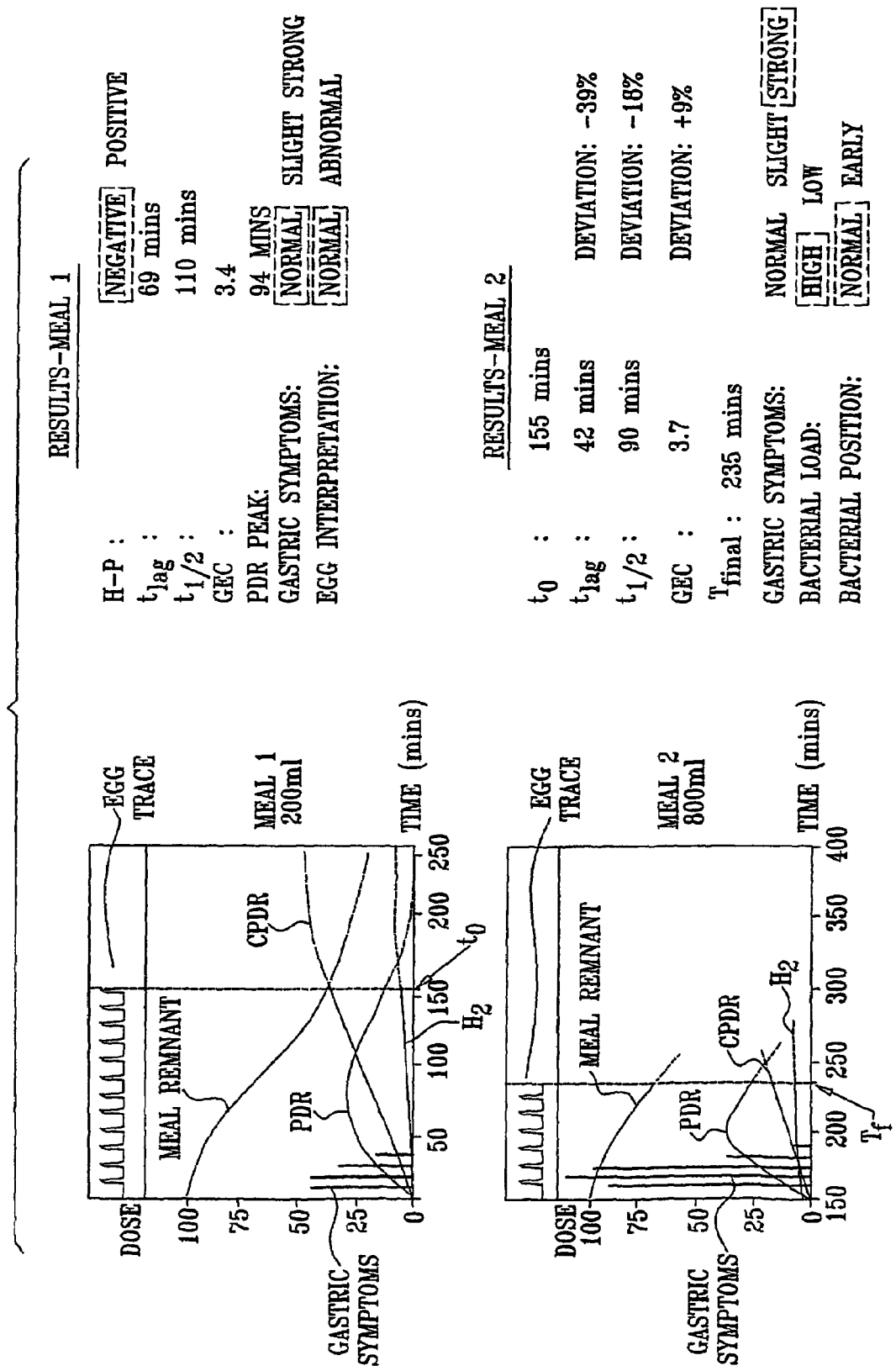

Reference is now made to FIGS. 5C and 5D, which are schematic illustrations of a breath tester, constructed and operative according to yet another preferred embodiment the present invention, which is capable of providing multi-functional gastric diagnosis information to the physician. Such a system enables the physician to perform the diagnostic routines illustrated in FIG. 1C, and even more, on a single instrument. The breath tester preferably both incorporates embodiments described in the present application, and in addition, utilizes external inputs from other tests to provide a comprehensive dyspepsia information management system. FIG. 5C shows a schematic block diagram of the component parts of the breath tester, while FIG. 5D shows a schematic representation of a preferred display output screen of such a system.

Reference is now made to FIG. 5C, which shows breath input I delivering breath, preferably in separate batches 1, 2, following the administration of successive meals, for analysis by gas analyzer I, which preferably analyzes the breath for labeled carbon dioxide content. From here, the analysis results are directed to gastric emptying rate and gastric accommodation (GE/GA) diagnosis processing modules, such as those shown in FIGS. 2E and 5A hereinabove. Additionally and preferably, the system also comprises a second gas analyzer II, which preferably analyzes the breath for hydrogen or methane content, and from where the results are directed to a diagnosis processing module for the detection of bacterial overgrowth, lactose intolerance, sugar malabsorption, or low GI motility, such as that shown in FIG. 14 hereinbelow. This processing module is known as the IBS diagnostic generator. The output information from the GE/GA and IBS diagnostic processors are input to the multi-functional gastro-intestinal diagnostic processor, which is responsible for sorting and assembling all of the output information for inputting to the display Additionally and preferably, further inputs are provided to the multi-functional gastro-intestinal diagnostic processor from other tests providing information about the subject's gastric condition. Amongst such tests are the results of a breath test for the detection of the presence of a *Helicobacter pylori* infection. This test can be performed after administration of the relevant labeled substrate for performing the test, using the same breath input as for the GE/GA tests and the same gas analyzer. However, to avoid interference with the results of the GE/GA tests, it should be performed at a different time to the GE/GA tests, preferably at least a few hours previously, and the results stored in the system memory.

Furthermore, the output from an electrogastrography (EGG) test can also be input to the processor and displayed on the display, such that the physician also has these results for review in assessing the subject's overall GI condition. In addition, an input of patient gastric symptoms can also be provided, as described in connection with the embodiment of FIG. 5A. Finally, other external devices providing useful GI functional information can also be input to the system, to provide as full a picture as possible for the physician.

Reference is now made to FIG. 5D, which illustrates a typical display output screen of the system shown in FIG. 5C. In the preferred example shown in FIG. 5C, the screen is divided into two sections, with the graphic outputs of the tests shown on the left hand side, and the results of processing these graphic outputs displayed as a table on the right hand side, though it is to be understood that any other suitable display arrangement may also be used without departing from the scope of the invention. There is shown a graphic outcome of a first low volume meal, already extrapolated to show gastric emptying parameters after convergence is achieved, with a dashed line indicating the curves extrapolated beyond the cut-off point of the test $t_0$. As is observed, the results of the first meal are plotted only until a clear indication of the values of the first meal gastric parameters has been obtained. The bottom graph shows a second meal in which curve analysis is in progress. The measurement curves for these two consecutive meals appear simultaneously and separately together with an estimation of the dumping curves and an estimation of the gastric emptying rate from the first meal.

In addition, a graphic representation of the graded gastric symptom level of the subject, as expressed and input by the subject himself, is shown in the form of a histogram, as a function of time from the moment of meal ingestion. Assessment of gastric symptoms during meal ingestion is useful in determining a subject's visceral sensitivity, also sometimes known as gastric sensation, which can determine whether the cause of the dyspeptic symptoms is related to the mechanical distress caused by the meal volume, or to the chemical composition of the test meal intake, such as for instance the fat content. Visceral sensitivity relates to visceral sensory function, as described, for instance, on page 27 of "Clinician's Manual on Managing Dyspepsia" by Gerald Holtman and Nicholas J. Talley, published by Life Science Communications, 2000. In a sub-set of patients who suffer from functional dyspepsia a decreased threshold for perception of gastric distention has been observed. Therefore by comparing the symptoms of the subject, it is possible to determine if the dyspeptic symptoms are associated with sensitivity to gastric distention or sensitivity to the chemical content of the meal.

As an example, if a significant symptomatic reaction is observed during the ingestion of meals of different volume, it is a sign of chemical content distress, regardless of whether the measurements also show a gastric accommodation dysfunction related to the meal size. This information is of clinical importance in determining the appropriate pharmacological treatment. In the case shown in FIG. 5D, the gastric symptoms recorded from the second and larger meal appear to be stronger, as often experienced with dyspeptic subjects who suffer from impaired gastric accommodation. This result is in-line with the faster emptying of the stomach, high volume meal, which is indicated by the deviation in some of the gastric emptying parameters displayed.

Additionally, this system can also measure and display an excretion curve of the hydrogen or methane level in the breath of the subject relative to the first and/or the second meal, as described in more detail hereinbelow. At the top of one of the screens, an EGG trace is displayed for viewing by the physician, and the also results of a previous test performed with the same system to detect active *Helicobacter pylori* infection in the GI tract of the subject.

This single instrument, is thus able to perform a comprehensive gastro-intestinal monitoring procedure on a single platform, displaying results for a number of functional GI disorders, and thus saving the subject multiple visits to the doctor's office.

It is to be understood that the gastric emptying and gastric accommodation breath tests described in the previously-mentioned preferred embodiments may be preferably performed by any suitable breath test apparatus, whether using an on-line, real time gas analyzer, or whether the subject's exhaled breaths are collected in individual bags and are then transferred to a remote gas analysis instrument, such as a mass spectrometer. Furthermore, those of the methods which are amenable thereto, can also be performed using scintigraphy, gamma imaging, CT, conventional X-ray imaging, MRI, ultrasound, or any other means known in the prior art for investigating and determining gastric functioning.

If breath tests are performed using an on-line, real-time breath test analyzer, such as the BreathID apparatus supplied by Oridion Medical Ltd., or as described in the above mentioned U.S. patent documents, then the second meal can be administered to the subject at the earliest possible time, either before the peak or after the peak, according to the requirements of the test and the response of the subject. Use of such apparatus thus may shorten the test in comparison with the other possible ways of applying the preferred methods of the present invention According to one preferred procedure for applying this first method using an on-line breath tester, after measurement of the baseline isotopic level, the subject is given 100 mg. of $^{13}$C-sodium acetate dissolved in 200 ml. of a standard high caloric liquid test meal, such as Ensure Plus®, or similarly available alternatives. Alternatively and preferably, the $^{13}$C-sodium acetate can be pre-dissolved in 5 ml-15 ml of water to facilitate its incorporation into the caloric liquid meal. After meal administration, breath samples are collected and analyzed by the breath analyzer at frequent intervals, or even quasi-continuously, and their DoB curve amplitude measured in real time, as described in the prior art. The resultant curve is fitted and extrapolated from the measured points, as previously explained, and the gastric emptying rate parameters are computed in real time, as well as their convergence towards their asymptotic values. A possible method to calculate the convergence of the gastric emptying parameters is to plot them as a function of time and to compute the derivative of the last measurement points, using the computing system that controls the breath analyzer, as described in the above-referenced U.S. patent documents. When the derivatives approximate to zero the convergence of the parameters is achieved. The above mentioned point in time $T_0$ at which the second test meal is administered, is assumed to be reached as soon as the convergence of $t_{1/2}$ and $t_{lag}$ is decided as definitely known, so that their values can be compared with those of the emptying curve of the second meal.

Figure 6:
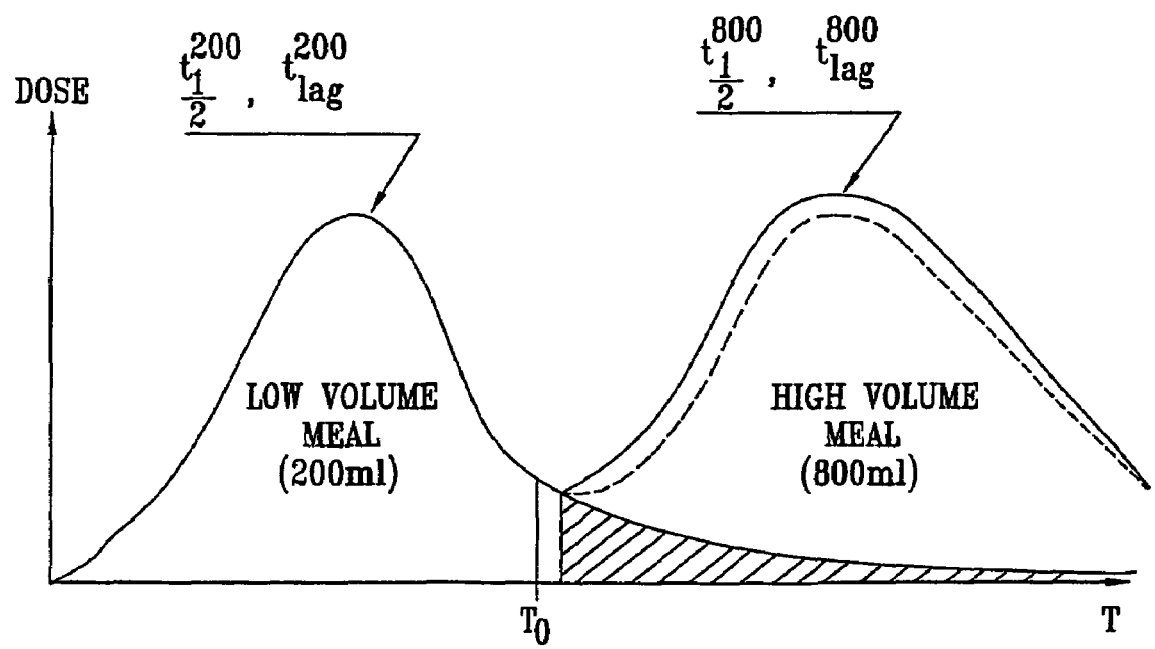
FIG. 6 illustrates schematically how compensation is made in the second meal curve for residual parts of the first meal still residing in the gastrointestinal tract, with isotopic $^{13}C$-cleavage products that have not been exhaled by the lungs yet.

According to the preferred embodiment wherein the second meal is also labeled, the second meal also preferably comprises 100 mg. of $^{13}$C-sodium acetate dissolved in 200 ml of a standard high caloric liquid meal, but diluted with an additional 600 ml of water. The $t_{1/2}$ and $t_{lag}$ parameters are now calculated for the second test meal from the time $T_0$ when it is administered. However, at least during the first period after administration of the second meal, a residual part of the first meal still resides in the gastrointestinal tract, with its isotopic $^{13}$C-cleavage products that have not been exhaled by the lungs yet. These residuals from the first meal would therefore interfere with the results obtained from the isotopically labeled second meal. Reference is made to FIG. 6, which illustrates schematically how this physiological interference is compensated for. As it is shown in FIG. 6, after computing the shape of the first curve, and extracting from it values of the $t_{1/2}$ and $t_{lag}$ parameters for the low volume meal, the curve is extrapolated beyond the time $\tau_0$ at which the second meal is administered, and the residual values of the extrapolated curve are subtracted from the measurement points to generate a corrected measurement curve from which the values of the $t_{1/2}$ and $t_{lag}$ parameters for the high volume meal are obtained. The actual measured curve is shown by the full line in FIG. 6, and the corrected curve by the dotted line.

The deviation between the set of parameters of the first meal and of the second meal is calculated. In individuals with a gastric accommodation disorder, the rate of emptying of the high volume second liquid meal is generally faster than for the first liquid meal. It is an indication of increased intra-gastric pressure, and therefore an indication of an accommodation problem. In a number of analyses performed, the emptying half-time of symptomatic patients was found to be at least 20% faster for the second meal. In addition, in these same test, a significant decrease in $T_{lag}$ (lag time) was observed in subjects with impaired accommodation.

Reference is now made to FIG. 7, which is a table showing the deviation of the gastric emptying parameters between a series of subjects, some showing abnormal gastric accommodation and some being asymptomatic. Results for the first method described hereinabove are shown on the left hand half of the table, labeled "Two meal procedure". These results are also compared with those obtained from an alternative preferred method, called the "Two test procedure", to be described hereinbelow.

It is seen that the lag phase deviation, expressed by the differences in the $t_{lag}$ parameter, is usually greater in symptomatic subjects. High values of $t_{1/2}$ and $t_{lag}$ in the first meal are also an indication of delayed gastric emptying.

In those embodiments where a high calorie liquid test meal is utilized, in a normal subject, a constant emptying rate is generally found, according to the rate of release of calories for passage to the digestive tract. Especially suitable meals for this purpose are those caloric drinks with a high percent of fats, such as the commercially available Ensure Plus® or Nutradrink® products. Such a meal forces the stomach to release its caloric content slowly into the small intestine. It also allows the utilization of similar amounts of labeled substrate, independently of the dilution resulting from the different volumes of the test meals.

Figure 8:
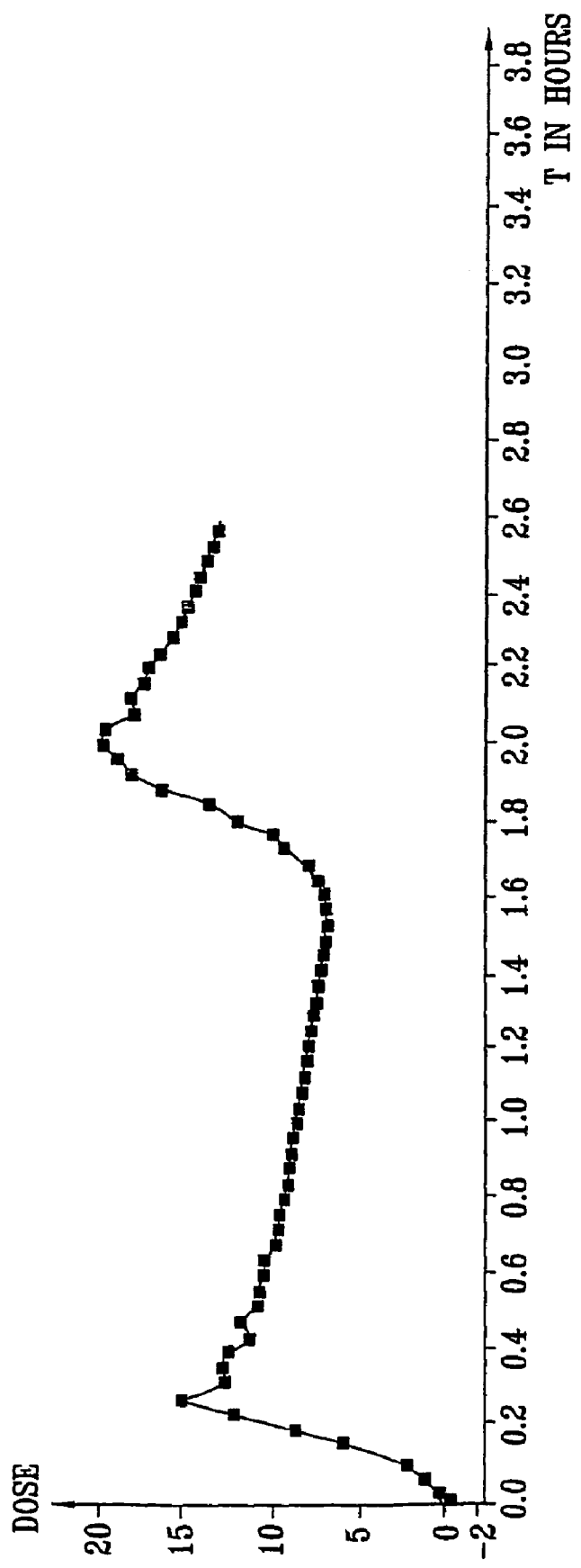
FIG. 8 shows schematic test results of an asymptomatic subject, performing a two-meal test, with a high volume water meal as the second meal.

When only water is utilized as the test meal, using 200 ml and 800 ml of water each with 100 mg. of sodium acetate, for the first and second meal respectively, the above-described tests lose some of their specificity. The test results of an asymptomatic subject, as shown in FIG. 8 indicate that the to, time after the high volume water meal was some 25% shorter than that after the low volume water meal, even though the subject was known to be normal, and $t_{lag}$ was unaltered. After performing a similar test with low volume and high volume Ensure Plus® test meals, the same subject showed very close values for both $t_{1/2}$, and $t_{lag}$ for the two volumes.

When citric acid is utilized to modulate gastric emptying rate, a significantly slower convergence of the parameters and also a lower specificity is generally found. This is thought to be because the physiological mechanism of the stomach in releasing its contents as a result of the pH of those contents is probably different from the calorific emptying mechanism. Furthermore, pH is affected by dilution, while total calorie count is not. Therefore different test meals amounts must be utilized for the different volumes.

According to further preferred embodiments of the present invention, there are provided kits for enabling the efficient and safe execution of the gastric accommodation tests of the present invention. In the preferred case of a breath test, the kit preferably comprises the required quantity or quantities of isotopically labeled marker material for adding to the meal or meals used in executing the test. In order to ensure correct usage of the meals and marker, a directions-for-use protocol (DFU) or a package insert is preferably included in the kit. This protocol can preferably include such instructions as the dilution procedures for the meals, if applicable, for the addition of the marker materials, and instructions for identifying or relating to the point in time when the second meal is to be taken, either according to the results of gastric emptying measured on the first meal, or where this is performed automatically by the gastric accommodation test system, according to the signal provided by the system, or after a pre-determined elapsed time, in those cases where the analysis is not done on-line. This protocol can also preferably include directions for the interpretation of the results of the test, which could preferably be the criteria for defining a set of parameter results as being normal, abnormal or borderline, and/or differences in sets of parameters as being representative of patients with normal, abnormal or borderline gastric accommodation, gastric emptying and visceral sensitivity. Alternatively and preferably, the kit could also include containers of the meal concentrates themselves, such as cans of Ensure® or the like, for producing the required meals by dilution. Alternatively and preferably, the kit could also include a breath collection device used for collecting the subject's breath.

B. The single meal method

In this preferred embodiment, a single liquid meal with a defined calorie content and containing a labeled marker preferably selected from those described above, is administered to the subject. The size of the liquid meal may preferably be 750 ml. or more, though as described below, smaller meal volumes of down to 100 ml and larger meal volumes of even up to 1.5 liters, may be used. The meal is designed, for instance by means of its low pH or its high calorific value, to ensure that it should remain in the stomach of a normal subject for a certain predetermined time x, such as 60 minutes, and have an emptying rate as defined by the half emptying time, $t_{1/2}$ of $\gamma$, such as 90 minutes. Upon breath test analysis, a Delta over Baseline curve is preferably traced and the curve of the liquid emptying though the stomach is determined from the outcome. The gastric emptying parameters are determined from this curve.

In subjects having a rate of emptying of the liquid meal faster than normal, this may be an indication of increased gastric pressure, and therefore an indication of an accommodation problem. A possible outcome of the breath test would thus be a change in the slope of the emptying curve.

Figure 9A:
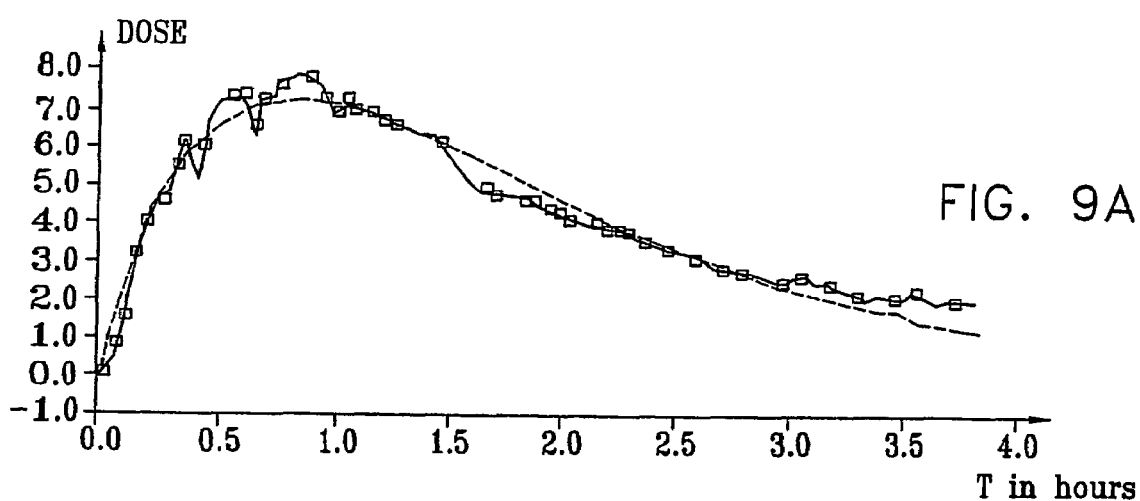
FIGS. 9A to 9C show schematic samples of gastric emptying curves obtained from single meal tests.
Figure 9B:
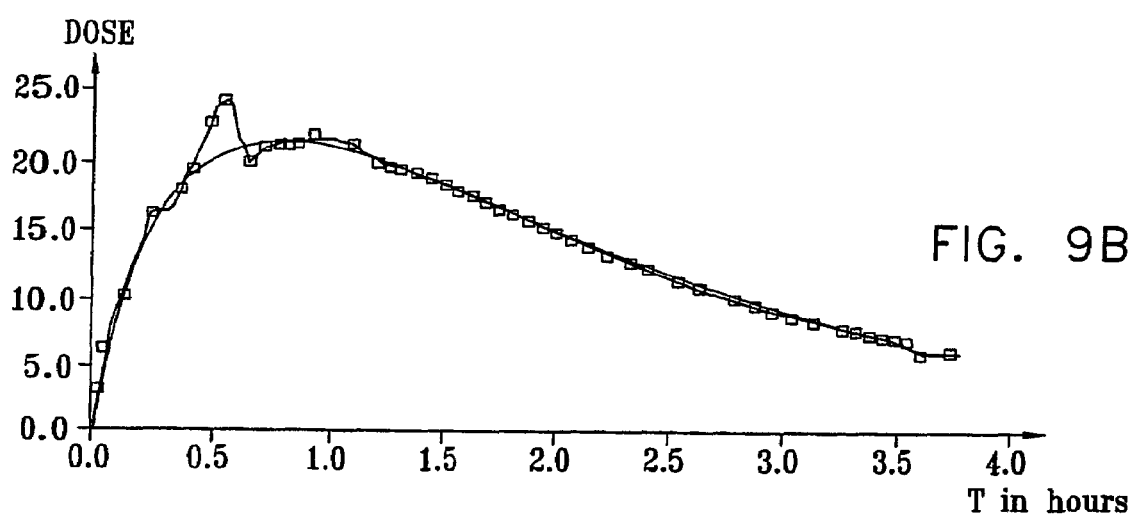

If results are not clear after this first test, the breath test may be repeated using the same meal but in a smaller volume, such as 100 ml, such that the meal is more concentrated. In this way, the effect of volume alone can be compared, as explained in the two test method hereinabove. Samples of curves from normal individuals after administration of low volume and high volume liquid test meals are shown in FIGS. 9A and 9B respectively. As is expected from a subject with normal gastric accommodation, the curve shapes are very similar, even though it is apparent from the dosage ordinate that the meal used in obtaining the results of FIG. 9B was significantly larger than that of FIG. 9A.

Figure 9C:
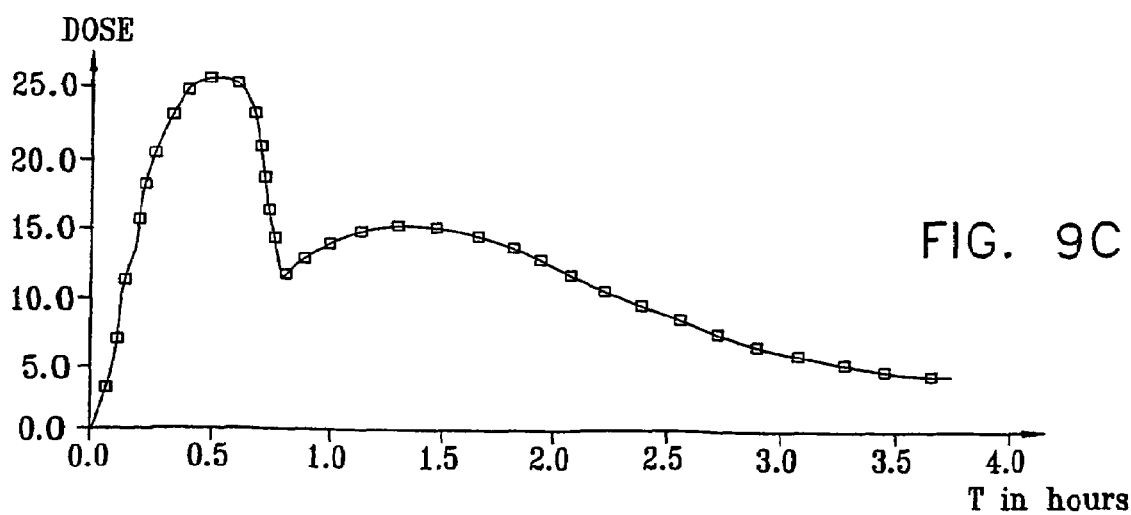

The single meal breath test described above provides results either by comparison of the extracted parameters with the accepted norms, or by repetition and comparison with a different volume meal, which is thus essentially a two meal test. Reference is now made to FIG. 9C, which shows the typical results from a further single meal test, indicative of a third type of result from which information about gastric accommodation disorders can be obtained. In this test, following administration of a high volume meal, such as that described in the embodiment of FIG. 9B, it is observed that the measured gastric emptying rate is initially higher than normal, as evidenced by the large and early peak of the dose curve. However, instead of a steady decline in the detected meal volume expelled from the stomach, a second and generally lower peak is observed, which then often is seen to decay at the expected normal rate as shown in FIGS. 9A and 9B. The result shown in FIG. 9C is typical of an impaired gastric accommodation condition which causes the stomach to initially expel the large meal at a high rate, from which section of the curve a first set of gastric emptying parameters can be extracted, typical of those pertaining to the large volume of the meal in the stomach of a subject with impaired gastric accommodation, and then, once the meal volume has reduced to lower levels, the gastric emptying becomes normal, and a second set of gastric emptying parameters can be extracted, typical of the small volume remaining in the stomach. The difference between corresponding ones of these two sets of gastric emptying parameters can be used to determine the presence and severity of the impaired gastric accommodation in the subject. In this respect, the physiology of the subject's gastric emptying function is operative to turn a single meal test effectively into a two meal test, since the gastric emptying function itself divides the meal emptying function into two separate phases, a high volume meal phase, and a low volume meal phase.

Similar results to those shown in FIG. 9C can be explained in terms of an impaired gastric relaxation mechanism operative on reception of a high volume meal, this condition being known as abnormal gastric accommodation reflex. In this condition, detection of two phases in the gastric emptying of a meal, and determination of the point in time between the phases may be used to indicate when stomach relaxation occurs following meal administration. Delay in the stomach relaxation accommodation process may indicate a pathological physiology function. It is to be understood, though, that the execution of this preferred embodiment of the present invention can be performed independently of the exact mechanism responsible for the resulting curve shape, and the actual or assumed mechanism is not meant to limit the scope of the invention.

C. The two test procedure

In this preferred embodiment of the methods of the present invention, the tests are essentially the same as those described in the two meal method described above, but are preferably performed on two different occasions, at times sufficiently spaced apart that the effects of the first meal, including effects right down the metabolic pathway of the labeled substrate, have essentially dissipated before the second meal is administered. Typically, the two test method is performed on two successive days, but where it is possible or desirable, a first test early in the morning followed by the second test later in the day is also an operable option. On each of these two separate occasions, a test meal is administered with an identically labeled substrate, but with a different volume. The parameters of the normal ranges of gastric emptying and the test curves are determined and the relative deviation between the parameters of the curves for each measurement with its specific test meal volume are calculated. This approach may provide greater confidence than using one test, with one type of meal alone.

According to one preferred embodiment of the two-test procedure, the tests are performed on the subject on two different days. On the first day, after a baseline isotopic breath measurement is taken, the subject is administered 100 mg. of $^{13}$C-sodium acetate dissolved in 200 ml of a standard high caloric liquid test meal, such as Ensure Plus®. Alternatively the $^{13}$C-sodium acetate can be initially dissolved into 5 ml-15 ml of water to facilitate its incorporation into the caloric liquid meal. After the meal administration, breath samples are repeatedly or virtually continuously collected by a breath analyzer and their DoB measured in real time, as is known in the art. The measurement curve is fitted to the results of the analyses, the gastric emptying rate parameters are computed therefrom in real time, and their asymptotic convergence values determined. On the second day, the same procedure is repeated, but the meal is amended, preferably by the addition of 600 ml. of water to the 200 ml. of standard high caloric liquid test meal with 100 mg. of $^{13}$C-sodium acetate. The gastric emptying rate parameters are again calculated for this second meal, and their deviation from those of the first meal calculated. Some typical test results for a symptomatic subject are shown in FIGS. 10A and 10B. In FIG. 10A, a 200 ml. high caloric test meal is administered on the next day to the same subject, and the value of $t_{1/2}$ is found to be 156 minutes. In FIG. 10B, an 800 ml. high caloric test meal is administered, and the value of $t_{1/2}$ is found to be 99 minutes, indicative of impaired gastric accommodation.

The above three described procedures have been described in terms of their implementation in the form of breath tests. However, it is to be understood that the concepts underlying the above-described methods for the measurement of gastric emptying parameters could also be performed by using different measurement methods other than those of breath testing. Such methods include, but are not meant to be limited to, the use of radioactive isotope tracking using $^{99}$Te, $^{14}$C or other labeled substrates, the use of ferromagnetic materials as markers to be tracked by MRI, the use of contrast materials in X-ray or CT methods, or the use of gas bubbles in ultrasound imaging, and alternative measurement methods using such techniques as magnetic resonance, gamma imaging or scintigraphy. Each of these methods, as known in their respective arts, and including those described according to the present invention, is characterized by its own sensitivity, specificity and convenience according to the meal utilized, population, clinical setting or the measurement equipment utilized.

New mathematical methods to determine gastric emptying rate have been currently proposed as alternatives to those already described in "$^{13}$C-Breath Test Modeling" by Tom Preston, East Kilbride. Department of Child Health and School of Veterinary Science, University of Glasgow. These methods are based on coupling different differential equations, or their equivalent, normalized to the Heaviside function, to each different metabolic or physiologic process, by means of a deconvolutive approach. Thus different parameters are obtained for each equation and are combined to obtain $t_{1/2}$ and $t_{lag}$ or their equivalents. These calculation methods differ from those known in the art only in their mathematical approach, and are based on the same breath test procedures or gastric emptying studies to provide an equivalent tool to scintigraphic analysis.

It has been observed in gastric accommodation procedures that the amount of labeled substrate does not affect parameters such as $t_{1/2}$ and $t_{lag}$, but only those related to the isotopic amplitude, such as the GEC, which shows mathematical homogeneity. It is therefore to be understood that the preferred methods of the present invention are not meant to be limited to any specific method of calculation of the gastric emptying rate parameters, but are applicable to alternative mathematical models also, such as that described above.

According to further preferred embodiments of the present invention, it is also proposed that it is of clinical significance to differentiate between either mechanical or chemical causes of dyspeptic symptoms in response to a meal. It is an objective of the present invention to provide this indication by means of recording the symptomatic response of the tested subject to the meals when the test is performed. Thus, in the Two Meal Procedure and Two Test Procedure methods for investigating patients with suspected defective gastric accommodation, if discomfort symptoms are observed only when a high volume test meal is administered, then the symptoms are an indication of a mechanical response to the volume. When discomfort symptoms are recorded with the small meal, or with both the small and the large meals, it is an indication of symptoms related to caloric or nutritional content or acidic composition of the meal, or what is termed "chemical stress sensitivity". There exist several methods to measure gastric discomfort symptoms, such as by the use of symptom questionnaires, clinical observation, facial recognition, biofeedback, as well known in the clinical arts. According to these preferred embodiments, a gastric symptomatic input can be entered into the system, preferably according to a scale of subjective gastric symptoms, with the recording being made after or during administration of a small volume meal, such as 100 to 350 ml., and a large volume meal, such as 500 to 1500 ml. Correlation between the subjective gastric symptom inputs and the objective gastric measurement outputs can then be performed, to generate a more complete clinical assessment of the subject's gastric accommodation, emptying and sensitivity.

These factors of gastric symptom can preferably be incorporated into the previously described systems, either by means of an input which is physician generated from the results of a subject questionnaire, or by means of a direct patient input to the data processing system. Such a gastric symptom input unit is shown in the apparatus depicted in FIG. 5A, providing an additional input to the gastric accommodation, emptying and sensitivity diagnostic output module. Since this is an optional feature, it is depicted in dashed outline.

Furthermore, according to another preferred embodiment of this invention, the above-described kit can preferably also include the elements of a questionnaire for applying to the subject, together with the marker materials or the meals themselves, and either in addition to or as an alternative to the test protocol instructions.

By the incorporation of the above described features of the measurement of gastric emptying, gastric accommodation and visceral sensitivity in one instrument, there is thus provided, according to further preferred embodiments of the present invention, a system that enables, in a single procedure, the assessment and differentiation of the physiological causes of dyspepsia in what is thought to be a majority of such cases. A single procedure is understood to mean, in relation to these preferred embodiments, a procedure that is performed on one day and using one system capable of correlating all of the data derived from the test. The use of such a single procedure thus removes day to day variability, and also the need for multiple test procedures, often performed on separate instruments. According to this preferred single procedure, successive ascertainments are made of the subject's dyspeptic symptoms at sequential times during passage of the meal through the subject's stomach. An ascertainment can also be made before administration of the meal.

According to these preferred embodiments, there is provided a dyspepsia evaluation breath test system, in which the gastric emptying, visceral sensitivity and gastric accommodation of a subject are accurately determined in a single test. Using this system, the gastric emptying is preferably determined from the first meal, the gastric accommodation from a comparison of the gastric emptying of the two meals, and the visceral sensitivity is evaluated from correlation of the dyspeptic symptoms as reported by the subject, with the volume and progress of the meals at various stages of the test. According to further preferred embodiments of the present invention, and based on the embodiments described hereinabove relating to each of the three supposed causes of the dyspepsia, there are also provided kits, methods and meals, for use in the evaluation of overall dyspeptic malfunctions in subjects.

In addition, this procedure could be coupled with other alternative motility parameters, such as an EGG, or physiological parameters such as lactose intolerance and bacterial overgrowth.

4. Bacterial Overgrowth Breath Test (BOBT)

Among other known causes of dyspepsia, IBS or gastrointestinal illness are bacterial overgrowth, which is the colonization of the small intestine or the upper gastrointestinal tract by colonic bacteria, lactose intolerance, malabsorptions of other sugars, or low gastrointestinal motility. With respect to bacterial overgrowth, the assessment of the level of these microorganisms outside the large intestine is usually performed either by means of gastroscopy, which is cumbersome, patient uncomfortable and depends on human interpretation, or by means of a hydrogen breath test (HBT). The HBT is performed by analysis of the breath before and after administering to a subject of a quantity of a marker sugar, such as lactulose, which is not broken down in the stomach. Bacteria break down the lactulose to produce hydrogen, a gas not produced by large organisms such as humans, as a natural result of the lactulose metabolism. Thus an increase in hydrogen level measured in the breath of a subject is an indication of bacterial activity. The time taken for the lactulose to reach the large intestine, as for other sugars which are not broken down in the stomach, is around 3 hours. Therefore an earlier hydrogen peak is a signal of bacterial overgrowth. Although hydrogen is the most common by-product used for breath testing of these GI disorders, methane can be produced when the ingested lactulose is metabolized by an alternative or additional bacteria present in the small intestine. According to other preferred embodiments of the present invention, such methane production can be used in these breath tests, in place of or in addition to hydrogen. Whenever the hydrogen breath test is mentioned in this application, it is to be understood that the test is meant to describe and to cover the methane breath test also, the differences being generally only in the gas detector used in the gas analyzer.

The main disadvantage of this prior art HBT is the need to identify the exact time during which the meal is passing through the small intestine. Because of variation in gastrointestinal transit times, both between different subjects and even in the same subject at different times, false negative and false positive diagnoses may arise.

Therefore to overcome these drawbacks, according to yet another preferred embodiment of the present invention, a breath test is proposed in which a substrate is administered, containing not only a substance such as lactulose which generates hydrogen in the presence of bacteria, but also containing a second isotopically labeled marker which is operative to indicate the location of the substrate within the intestinal tract. The hydrogen production is measured to indicate the fermentation action of bacterial flora, if any, and a second measurement of the decomposition products of the second marker is typically made at the same time as the measurement of the hydrogen output. The second measurement may preferably be the measurement of labeled $CO_2$ produced as the result of metabolism by the subject of a labeled carbon-containing substrate.

According to a preferred embodiment of the present invention, a $H_2$ detector such as an electrochemical spirometer or a gas chromatographer is incorporated in an isotopic gas analyzer being part of a breath test apparatus. Preferably, sample gases are collected in a control range of $CO_2$ concentrations by means of an intermediate cell, as described in the prior art.

Several different types of substrate may preferably be used to check both $H_2$ production in the small or large intestine, and the passage of the substrate through the intestines. According to a first preferred method of performing this breath test, a relatively large amount of glucose, lactose, sorbitol or lactulose, such as 100 g, are administered to the subject, together with a relatively small amount of $^{13}C$-labeled substrate that is rapidly absorbed or metabolized by the body in the intestine such as 100 mg. of glucose or sodium acetate or microencapsulated bicarbonate, for measurement of labeled $CO_2$ production. The glucose is absorbed and rapidly metabolized by the patient's body only when it reaches the small intestine, at which point it can be detected as labeled $CO_2$ in the subject's breath. The glucose can also be metabolized by bacteria, which is detected as $H_2$ in the breath. If the gaseous peaks of $^{13}CO_2$ and $H_2$ are correctly separated in time, in that the $^{13}CO_2$ peak occurs at least a predetermined time before the $H_2$, this indicates that the location of the subject's bacterial population is normal. This situation is illustrated in the schematic breath test results shown in FIG. 11. If, on the other hand, the $H_2$ peaks at a time close to the $^{13}CO_2$ peak, it indicates the presence of bacterial overgrowth in the small intestine, as shown schematically in FIG. 12. It should be noted that the "peak" of the hydrogen exhalation if far broader and long lasting than that of the $^{13}CO_2$ peak, and references to the $H_2$ peak as such, and its temporal position relative to the $^{13}CO_2$ peak, and as claimed, are to be thus qualified. Indeed, in most practical cases, instead of measurement of the "peak" position of the hydrogen, a measurement of $H_2$ exhalation is determined by the position at which the hydrogen exhalation achieves a certain level above the baseline level.

In a normal individual, the glucose is absorbed and metabolized by the body in the small intestine. Any remaining glucose will be available in the large intestine to provide a detectable hydrogen peak upon bacterial metabolism. In some instances, however, not enough glucose will remain to be passed to the large intestine to provide a detectable hydrogen peak from bacterial metabolism in a normal subject. In this case, a sugar which does not break down, such as lactulose, is included as a test substrate.

Figure 13:
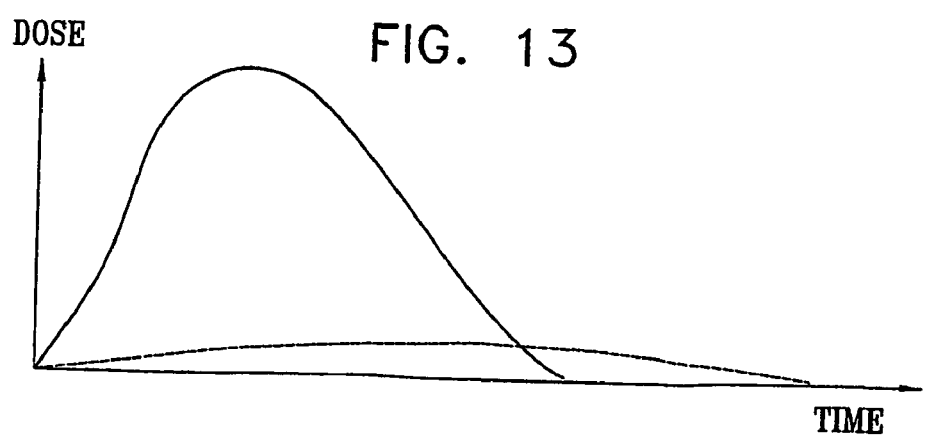

In another example, 100 mg. of a $^{13}C$ labeled substrate is administered together with a dedicated test substrate for a bacterial overgrowth hydrogen breath test, such as 10 grams of lactulose. As mentioned above, if the $^{13}CO_2$ peaks significantly before the $H_2$ this indicates that the location of the patient's bacterial population is normal, as shown schematically in FIG. 11. If the $H_2$ "peaks" at around the same time as the $^{13}CO_2$ peak, it indicates the presence of bacterial overgrowth in the small intestine, as shown schematically in FIG. 13. In this example, however, the presence of a non-breakdownable sugar such as lactulose as a test substrate ensures that a hydrogen peak will be detected, whether in the small intestine in a subject with bacterial overgrowth, or in the large intestine of a normal subject.

$^{13}CO_2$ originating from the known metabolism of the $^{13}C$-labeled substrate, is a marker peak to determine the point which the meal has reached in the gastrointestinal tract, and therefore, overcomes differences in digestion speed due to different metabolic dynamics, or due to the clinical state of the subject. This preferred method therefore overcomes the prior art disadvantage of intra- and inter-patient variation in gastrointestinal transit times.

According to further preferred embodiments of the present invention, the joint use of a hydrogen and a $CO_2$ marker in the ingested substrate also provides a method to determinate accelerated or delayed orocecal transit time. This is the time between the oral administration of the food and its arrival at the colon, where the colonic bacteria ferment the sugars. This process could be characterized by a high peak of hydrogen with a low labeled $CO_2$ production.

Other alternatives tests meals include, but are not limited to, labeled sodium acetate, sodium octanoate, glucose, a probe such as acetyl leucine, or a microencapsulated labeled substrate, together with a relatively large amount such as 70-100 g of unlabeled glucose, or 10 g of lactulose.

According to yet further preferred embodiments of the methods of the present invention, these substrates, provided in large amount, could be incorporated into a micro-encapsulation means, designed to allow their release only in the alkaline intra-intestinal media. This enables an improvement to be achieved in the accuracy in time of the test. Alternatively, the two components can be provided separately in the same meal, this being a particularly simple method of application. Single labeled substrates and dual/single microencapsulated markers have the advantages over the prior art that the absorption and metabolization by the body and/or bacterial fermentation are produced simultaneously in the GI tract.

Alternatively and preferably a microencapsulated formulation, which is breakdownable at the colon, containing a labeled substrate having rapid release, such as bicarbonate could be utilized to show orocecal gastric time.

Figure 12:
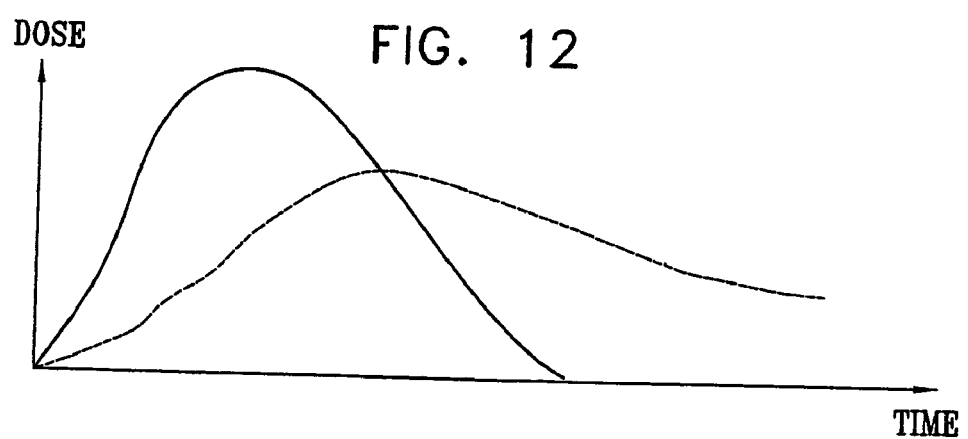

According to another preferred embodiment of the present invention, there is provided a method to improve the accuracy of and to shorten the duration of the lactose breath test (LBT), as well other sugar malabsorption breath tests, such as fructose or maltose or sucrose intolerance. It is believed that lactose intolerance occurs in 25% of the general population and is characterized by the low availability in the body of lactase, the enzyme which metabolizes the lactose in milk into glucose and galactose, for utilization by the body. As a consequence of this lactase deficiency, the unmetabolized lactose is fermented by colonic bacteria, producing detectable $H_2$. Simultaneous measurement of $^{13}CO_2$ and $H_2$ after $^{13}C$-lactose ingestion has been proposed for diagnosing lactose-intolerance, to detect such absorption of the unmetabolized lactose in the colon. Unfortunately, $1^3C$-labeled lactose is expensive and not easily available, making this an unattractive method of testing. The production of naturally $^{13}C$-labeled lactose has been suggested, by feeding milk-producing cows with $^{13}C$-enriched feed, which is reasonably cheaply available. However, the enrichment levels of such milk are too low to produce acceptable results and their variability is too high for standardization. There is thus provided, according to another preferred embodiment of the present invention, a method of providing a dual meal for detecting lactose intolerance. The dual meal comprises natural lactose, together with a labeled marker substrate, such as $^{13}C$-labeled xylose, a sugar which is mainly absorbed only when it gets to the colon, and which is readily available at low cost. Thus after ingestion of the dual meal, if the $^{13}CO_2$ is detected approximately at the same time as $H_2$, as shown in FIG. 12, it is a sign that the lactose has not been absorbed in the small intestine, due to the absence of lactase enzyme, but has reached the colon together with the labeled lactulose. If on the other hand, no $H_2$ is detected with the $^{13}CO_2$, this is a sign that the lactose has been correctly absorbed in the small intestine, and that the subject does not suffer from lactose intolerance. Additionally, the use of this meal enables the test time to be shortened, since it is known that the $H_2$ peak is expected shortly after the $^{13}CO_2$ peak if there is a deficiency of endogenous lactase, such that there is no need to wait an extended time to see whether an $H_2$ peak appears or not.

Figure 11:
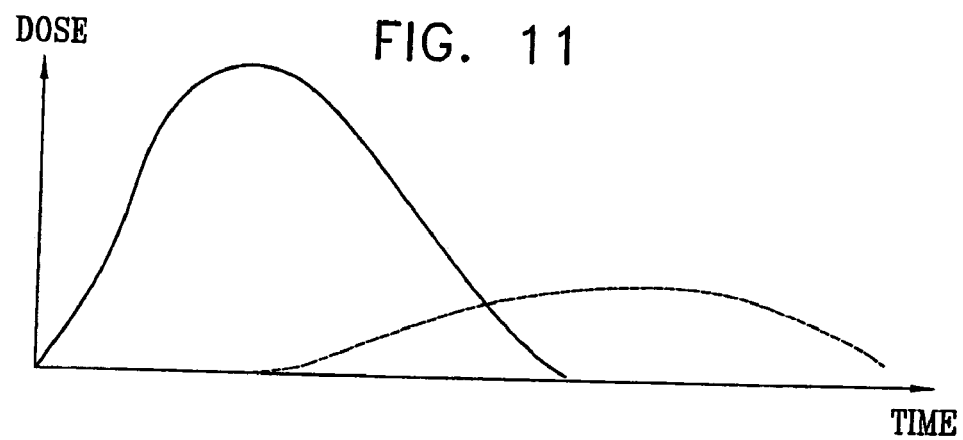
FIGS. 11 to 13 are schematic examples of curves obtained, each showing both a hydrogen peak and an isotopically labeled carbon dioxide peak, to illustrate the results obtained from subjects with different IBS disorders, including bacterial overgrowth and sugar malabsorbtions.

According to yet another preferred embodiment of the present invention, a dual meal comprising lactose and a marker substrate absorbed in the small intestine, such as $^{13}C$-labeled sodium acetate, could be used to determine the presence of either sugar malabsorption, such as lactose intolerance or of bacterial overgrowth or of both. If the subject suffers from bacterial overgrowth but not from lactose intolerance, most of the lactose is rapidly absorbed in the small intestine, but a small quantity generates hydrogen because of contact with the bacterial overgrowth there. As a consequence, a small $H_2$ peak occurs approximately at the same time as the $^{13}CO_2$ peak as the meal is passing through the small intestine, as shown in FIG. 11. If on the other hand, the subject has lactose intolerance, then a large $H_2$ peak occurs when essentially all of the lactose reaches the bacteria in the colon, and this occurs later than the $^{13}CO_2$ peak, produced during passage of the labeled sodium acetate through the small intestine, as previously explained. If the subject suffers from both disorders, then the absence of a lactose absorption mechanism results in all of the lactose being available in the small intestine for exposure to the bacterial overgrowth therein, and the result is a large $H_2$ peak occurring at the same time as the $^{13}CO_2$ peak.

Alternatively a labeled substrate that is metabolized at the colon such as xylose or microencapsulated bicarbonate could be utilized together with the lactose. In such a case, an early hydrogen peak and a later peak of the labeled substrate is a sign of bacterial overgrowth. The two peaks concurrently is a sign of lactose intolerance.

According to yet another preferred embodiment of the present invention, $^{13}C$-labeled glucose, sodium acetate or another $^{13}C$-labeled material, could be utilized in a solid/liquid test meal including glucose or lactulose for the combined assessment of gastric accommodation, gastric emptying and bacterial overgrowth in one test at the same opportunity, thereby reducing the number of visits which the patient has to make to the clinic.

The bacterial overgrowth breath test can be summarized as follows:

1. A meal is labeled with a $^{13}C$ labeled material that is absorbed in the small intestine and produces a $CO_2$ peak as soon as the meal passes through the small intestine
2. The same meal produces an $H_2$ peak in a Breath Test (BT) when it gets to normal bacterial concentrations in the large intestines.

3. The use of a non-broken down sugar, such as lactulose, determines bacterial overgrowth according to the time taken for the H2 peak to develop.
4. Perform the BT to detect both $CO_2$ and $H_2$ peaks. If the peaks are correctly separated in time, the patient's bacterial location is normal. If the $H_2$ peaks at a time close to the $CO_2$ peak, it indicates the presence of bacterial overgrowth in the small intestine.
5. An advantage is that by using $CO_2$ as a marker peak to determine the location of the meal in the GI tract, it is possible to overcome differences in digestion speed due to different metabolisms, or to the clinical state of the patient.

Figure 14:
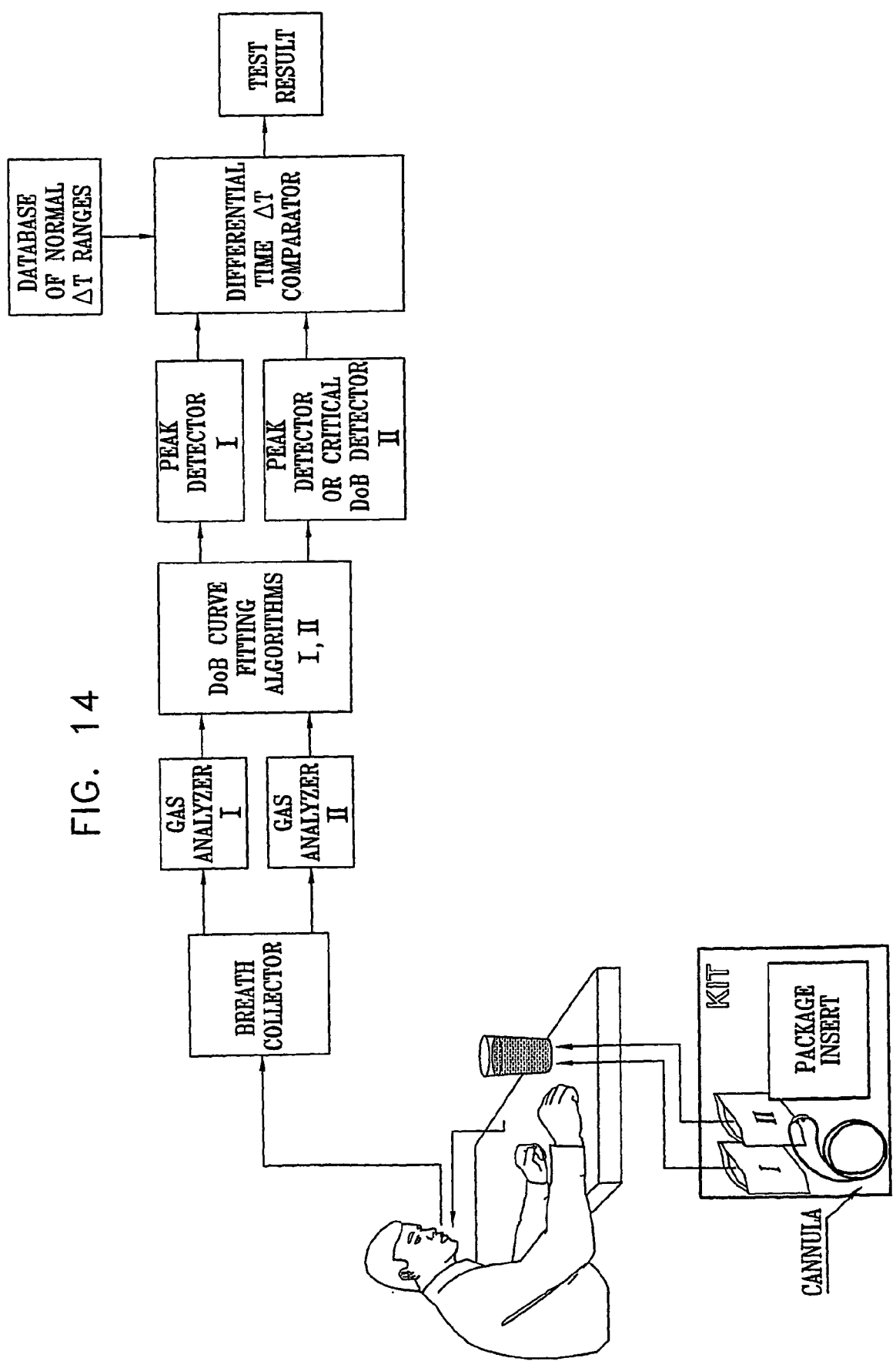
FIG. 14 schematically illustrates a system, according to another preferred embodiment of the present invention, for performing breath tests for the detection of bacterial overgrowth or various GI intolerances.

Reference is now made to FIG. 14, which is schematic representation of a breath test system for the detection of bacterial overgrowth, lactose intolerance, sugar malabsorption, or low GI motility, constructed and operative according to a preferred embodiment of the present invention. After administration of the relevant meal or portion containing the breath test substrates, according to the particular test to be executed, as expounded in the above-described embodiments, the exhaled breaths of the subject are collected at the inlet to the system, and passed to dual gas analyzers. One of these analyzers is preferably of the type which detects and measures the quantity of hydrogen and/or methane in the breaths, and the other is preferably an isotopic ratio analyzer, which determines the ratio in the exhaled breaths of the labeled isotope from the ingested substrate to its equivalent naturally occurring isotope. These analyses are performed repetitively or even virtually continuously for the duration of the test, and the results of each of these analyses are preferably input to a computing module which uses a curve fitting algorithm, such as one of the numerous types known in the art, for fitting the data to a DoB curve, separately for the hydrogen or methane levels, and for the isotopic ratio. Alternatively and preferably to the DoB, any of the other representations of the dose measured in the exhaled breaths, such as the PDR, may be used, as described hereinabove,. These curves, or the data constituting them is then preferably input to a data analyzer, which detects the region of the peaks of the curves, as a function of elapsed time from administration of the test meals. In the case of the hydrogen or methane data, it is not uncommon that no meaningful peak can be detected, because a very broad and low plateau-shaped curve is obtained. For this reason, the hydrogen or methane analyzer unit is preferably pre-programmed that when no meaningful peak can be extracted from the data, the algorithm alternatively detects the point in time when the hydrogen or methane level exceeds a predetermined level over the threshold, and this point in time is used as a basis for defining the presence of a hydrogen or methane "peak". The differential time comparator then preferably calculates the difference in time of occurrence of the two peaks, compares the resulting difference with a database of normal ranges of this time difference, and generates a test result for the breath test, based on the comparison of any measured time difference with the expected norms.

Furthermore, according to further preferred embodiments of the present invention, there are provided kits for enabling the efficient and safe execution of these described breath tests. The kit preferably comprises the required quantities of the two separate component substrate materials used in executing the particular test for which that kit is supplied. In order to ensure correct usage of the substrates and/or markers, a directions-for-use protocol (DFU) or a package insert is preferably included in the kit. This protocol can preferably include such instructions as the preparation procedures for the meals, if applicable, and instructions for the addition of the marker materials if applicable. This protocol can also preferably include directions for the interpretation of the results of the test, which could preferably be the criteria for defining a set of time differential results as being normal, abnormal or borderline.

It will be appreciated by persons skilled in the art that the present invention is not limited by what has been particularly shown and described hereinabove. Rather the scope of the present invention includes both combinations and subcombinations of various features described hereinabove as well as variations and modifications thereto which would occur to a person of skill in the art upon reading the above description and which are not in the prior art.

We claim:

1. A method for the evaluation of the gastric accommodation in a subject, comprising the steps of:
    administering to said subject at least one meal comprising at least one constituent operative to cause retention of said at least one meal in the stomach of a subject, said at least one meal having a predetermined volume;
    performing at least two measurements of either one of the slope of the gastric emptying curve and a gastric emptying parameter of said at least one meal after different volumes of said meal have exited the stomach of the subject; and
    evaluating the gastric accommodation of the subject from said measurements of either one of the slope of the gastric emptying curve and a gastric emptying parameter as a function of the volume of said meal having exited the subject's stomach.

2. A method according to claim 1 wherein said at least one meal is one meal.

3. A method according to claim 1 wherein at least one of said at least two measurements is performed on a liquid emptying phase of one of said at least one meal from the stomach of the subject.

4. A method according to claim 1 wherein said at least one meal is at least two meals, and one of said at least two measurements is performed on a first one of said at least two meals, and a second one of said at least two measurements is performed on a second one of said at least two meals.

5. A method according to claim 4 wherein said first one of said at least two meals is larger than the second one of said at least two meals.

6. A method according to claim 4 wherein the volume of said second one of said at least two meals is larger than that of the first one of said at least two meals.

7. A method according to claim 6 wherein the volume of said second one of said at least two meals is at least twice that of said first one of said at least two meals.

8. A method according to claim 1 wherein one meal of said at least one meal comprises a marker which is detected after leaving the stomach of said subject.

9. A method according to claim 8 and wherein said marker is detected by its presence in the exhaled breath of said subject.

10. A method according to claim 8 and wherein said marker is detected by its presence within the body of said subject.

11. A method according to claim 10 and wherein said marker is detected by its presence in the gastrointestinal tract of said subject.

12. A method according to claim 1, wherein said at least one meal comprises at least one of:
    a caloric value of at least 150 kcalories,
    a lipid content of at least 5%;

a carbohydrate content of at least 10%;

a protein content of at least 5%; and a pH value of less than 3.

13. A method according to claim 12 wherein said carbohydrate is glucose.

14. A method for the evaluation of the gastric accommodation in a subject, comprising the steps of:
- administering to said subject a first liquid meal comprising a first predetermined volume;
- administering to said subject, after said first liquid meal has begun emptying from the stomach of the subject, a second liquid meal comprising a second predetermined volume;
- measuring at least one gastric emptying characteristic of said first meal and of said second meal; and
- evaluating the gastric accommodation of the subject according to the deviation between said at least one gastric emptying characteristic of said second meal and said at least one gastric emptying characteristic of said first meal.

15. A method according to claim 14 and wherein said second predetermined volume is sufficient to cause gastric distension in said subject.

16. A method according to claim 14 and wherein said second predetermined volume is at least 500 milliliters of liquid.

17. A method according to claim 14 and wherein at least one of said first and said second liquid meal has a predetermined gastric retention characteristic arising from at least one of a predetermined pH, a predetermined calorific value and a predetermined composition.

18. A method according to claim 17 and wherein said predetermined gastric retention characteristic arises from at least one of a pH is less than 3.0, a calorific value of at least 150 kilocalories, and an isotonic predetermined composition.

19. A method according to claim 14 and wherein said administering to said subject of said second liquid meal is performed as soon as said at least one gastric emptying characteristic of said first meal is determined.

20. A method according to claim 14 and wherein said administering to said subject of said second liquid meal is performed after a time when essentially all physiological effects of said first meal on said subject have terminated.

21. A method according to claim 20 and wherein said administering to said subject of said second liquid meal is performed on a successive day to said first meal.

22. A method according to claim 14 wherein at least one of said first and second liquid meals comprises a marker which is detected after leaving the stomach of said subject.

23. A method according to claim 22 and wherein said marker is detected by its presence in the exhaled breath of said subject.

24. A method according to claim 22 and wherein said marker is detected by its presence within the body of said subject.

25. A method according to claim 22 and wherein said marker is detected by its presence in the gastro-intestinal tract of said subject.

26. A method according to claim 14 and wherein said gastric emptying characteristic is determined by one of a breath test, scintigraphy, an X-ray, computerized tomography, gamma imaging and an ultrasound method.

27. A method for the evaluation of at least two of gastric accommodation, gastric emptying and visceral sensitivity of a subject, comprising the steps of:
- administering to the subject a first liquid meal comprising a first predetermined volume;
- administering to the subject, after said first liquid meal has begun emptying from the stomach of the subject, a second liquid meal comprising a second predetermined volume;
- determining the gastric emptying rates of said first and second meal; utilizing said gastric emptying rates to determine the gastric accommodation level of the subject; ascertaining the level of perceived dyspeptic symptoms of the subject at least upon administration of said first and said second meal; and
- correlating said level of perceived dyspeptic symptoms of the subject with the volumes of said first and second meals to determine the level of visceral sensitivity, such that at least two of gastric accommodation, gastric emptying and visceral sensitivity of a subject may be determined in a single procedure.

28. A method according to claim 27, and wherein said first predetermined volume and said second predetermined volume are different.

* * * * *